(12) United States Patent
White et al.

(10) Patent No.: US 8,404,694 B2
(45) Date of Patent: Mar. 26, 2013

(54) AURORA KINASE MODULATORS AND METHOD OF USE

(75) Inventors: Ryan White, Somerville, MA (US); Jason Brooks Human, Boston, MA (US)

(73) Assignee: Amgen Inc., Thousand Oaks, CA (US)

(*) Notice: Subject to any disclaimer, the term of this patent is extended or adjusted under 35 U.S.C. 154(b) by 21 days.

(21) Appl. No.: 12/933,400

(22) PCT Filed: Mar. 19, 2009

(86) PCT No.: PCT/US2009/001785
§ 371 (c)(1),
(2), (4) Date: Nov. 30, 2010

(87) PCT Pub. No.: WO2009/117157
PCT Pub. Date: Sep. 24, 2009

(65) Prior Publication Data
US 2011/0065709 A1    Mar. 17, 2011

Related U.S. Application Data

(60) Provisional application No. 61/070,333, filed on Mar. 20, 2008.

(51) Int. Cl.
*A01N 43/90* (2006.01)
*A61K 31/519* (2006.01)
*C07D 487/00* (2006.01)

(52) U.S. Cl. ................................ 514/259.3; 544/281

(58) Field of Classification Search .................. None
See application file for complete search history.

(56) References Cited

U.S. PATENT DOCUMENTS

| | | | |
|---|---|---|---|
| 6,143,764 A | 11/2000 | Kubo et al. | |
| 6,903,101 B1 | 6/2005 | Dumas | |
| 6,919,338 B2 | 7/2005 | Mortlock et al. | |

FOREIGN PATENT DOCUMENTS

| | | |
|---|---|---|
| EP | 1752457 A1 | 2/2007 |
| WO | 9713771 A1 | 4/1997 |
| WO | 9802434 A1 | 1/1998 |
| WO | 9802437 A1 | 1/1998 |
| WO | 0050405 A1 | 8/2000 |
| WO | 0071129 A1 | 11/2000 |
| WO | 0110859 A1 | 2/2001 |
| WO | 0121597 A1 | 3/2001 |
| WO | 0194353 A1 | 12/2001 |
| WO | 200649 A1 | 1/2002 |
| WO | 02092087 A1 | 11/2002 |
| WO | 03055491 A1 | 7/2003 |
| WO | 03082208 A2 | 10/2003 |
| WO | 03082289 A1 | 10/2003 |
| WO | 2004000833 A1 | 12/2003 |
| WO | 2004016612 A1 | 2/2004 |
| WO | 2004037814 A1 | 5/2004 |
| WO | 2004039774 A1 | 5/2004 |
| WO | 2005030144 A2 | 4/2005 |
| WO | 2005047279 A1 | 5/2005 |
| WO | 2005118572 A1 | 12/2005 |
| WO | 2005121125 A1 | 12/2005 |
| WO | 2006085330 A1 | 8/2006 |
| WO | 2007084815 A1 | 7/2007 |
| WO | 2007087276 A1 | 8/2007 |
| WO | 2008124083 A1 | 10/2008 |

OTHER PUBLICATIONS

R. Giet and C. Prigent, J. Cell. Sci., 112:3591-3601 (1999).
Y. Miyoshi et al., Int. J. Cancer, 92:370-373 (2001).
Angew. Chem. Int. Ed. 2003, 42, 5993-5996.
Garnier, E.; Andoux, J.; Pasquinet, E.; Suzenet, F.; Poullain, D.; Lebret, B.; Guillaumet, G. J. Org. Chem. 2004, 69, 7809.

*Primary Examiner* — Jeffrey Murray
(74) *Attorney, Agent, or Firm* — G. Prabhakar Reddy

(57) ABSTRACT

The present invention relates to chemical compounds having a general formula I

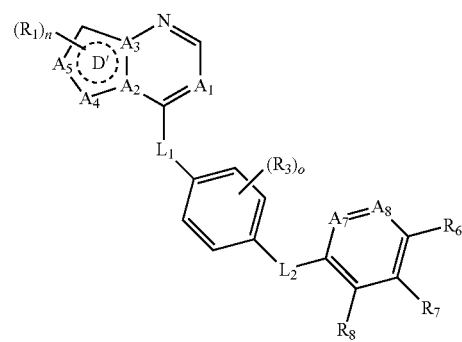

wherein $A^{1\text{-}5 \text{ and } 7\text{-}8}$, D', $L^1$, $L^2$, $R^1$, $R^3$, $R^{6\text{-}8}$, n and o are defined herein, and synthetic intermediates, which are capable of modulating the activity of Aurora kinase proteins and, thereby, influencing various disease states and conditions related to the activities of Aurora kinases. For example, the compounds are capable of influencing the process of cell cycle and cell proliferation to treat cancer and cancer-related diseases. The invention also includes pharmaceutical compositions, including the compounds, and methods of treating disease states related to the activity of Aurora kinase.

11 Claims, No Drawings

AURORA KINASE MODULATORS AND METHOD OF USE

RELATED APPLICATIONS

This application is a US national stage application via 35 USC §371(c) of PCT/US2009/001785, filed on Mar. 19, 2009, which PCT application claims the benefit of U.S. Provisional Application No. 61/070,333, filed Mar. 20, 2008, both specifications of which are hereby incorporated herein by reference in their entireties.

FIELD OF THE INVENTION

The invention relates to the field of pharmaceutical agents and, more specifically, is directed to compounds and compositions useful for modulating Aurora kinase, and to uses and methods for managing cell proliferation and for treating cancer.

BACKGROUND OF THE INVENTION

Cancer is one of the most widespread diseases afflicting mankind and a major cause of death worldwide. In an effort to find an effective treatment or a cure for one or more of the many different types of cancer, over the last couple of decades, numerous groups have invested a tremendous amount of time, effort and financial resources. However, to date, of the available cancer treatments and therapies, only a few offer any considerable degree of success.

Cancer is often characterized by unregulated cell proliferation. Damage to one or more genes, responsible for the cellular pathways, which control progress of proliferation through the cell cycle, typically causes the loss of normal regulation of cell proliferation. These genes code for various proteins, which participate in a cascade of events, including protein phosphorylation, leading to cell-cycling progression and cell proliferation. Various kinase proteins have been identified, which play roles in the cell cycling cascade and in protein phosphorylation in particular.

One class of proteins found to play a part in cell cycling and, therefore, cell proliferation is the Aurora kinase family of proteins. Aurora kinases are enzymes of the serine/threonine kinase family of proteins, which play an important role in protein phosphorylation during the mitotic phase of the cell cycle. There are three known members of the Aurora kinase family, Aurora A, Aurora B and Aurora C, also commonly referred to as Aurora 2, Aurora 1, and Aurora 3, respectively.

The specific function of each Aurora kinase member in mammalian cell cycle has been studied. Aurora-A is localized to the centrosome during interphase and is important for centrosome maturation and to maintain separation during spindle assembly. Aurora-B localizes to the kinetochore in the G2 phase of the cell cycle until metaphase, and relocates to the midbody after anaphase. Aurora-C was thought to function only in meiosis, but more recently has been found to be more closely related to Aurora-B, showing some overlapping functions and similar localization patterns in mitosis. Each aurora kinase appears to share a common structure, including a highly conserved catalytic domain and a very short N-terminal domain that varies in size. (See R. Giet and C. Prigent, J. Cell. Sci., 112:3591-3601 (1999)).

Aurora kinases appear to be viable targets for the treatment of cancer. Aurora kinases are overexpressed in various types of cancers, including colon, breast, lung, pancrease, prostate, bladder, head, neck, cervix, and ovarian cancers. The Aurora-A gene is part of an amplicon found in a subset of breast, colon, ovarian, liver, gastric and pancreatic tumors. Aurora-B has also been found to be overexpressed in most major tumor types. Overexpression of Aurora-B in rodent fibroblasts induces transformation, suggesting that Aurora-B is oncogenic. More recently, Aurora-B mRNA expression has been linked to chromosomal instability in human breast cancer. (Y. Miyoshi et al., Int. J. Cancer, 92:370-373 (2001)).

Further, inhibition of one or more of the Aurora kinases by several parties has been shown to inhibit cell proliferation and trigger apoptosis in several tumor cell lines. Particularly, inhibition of Aurora has been found to arrest cell cycling and promote programmed cell death via apoptosis. Accordingly, there has been a strong interest in finding inhibitors of Aurora kinase proteins.

Thus, the inhibition of Aurora kinases has been regarded as a promising approach for the development of novel anti-cancer agents. For example, WO 04/039774 describes aza-quinazolinones for treating cancer via inhibition of Aurora kinase, WO 04/037814 describes indazolinones for treating cancer via inhibition of Aurora-2 kinase, WO 04/016612 describes 2,6,9-substituted purine derivatives for treating cancer via inhibition of Aurora kinase, WO 04/000833 describes tri- and tetra-substituted pyrimidine compounds useful for treating Aurora-mediated diseases, WO 04/092607 describes crystals useful for screening, designing and evaluating compounds as agonists or antagonists of Aurora kinase and U.S. Pat. No. 6,919,338 and WO 03/055491 each describe substituted quinazoline derivatives as inhibitors of Aurora-2 kinase.

BRIEF DESCRIPTION OF THE INVENTION

The present invention provides a new class of compounds useful for modulating one or more of the Aurora kinase enzymes and for treating Aurora kinase-mediated conditions and/or diseases, including cancer. In one embodiment of the invention, the compounds, including pharmaceutically acceptable salts thereof, are generally defined by Formula I

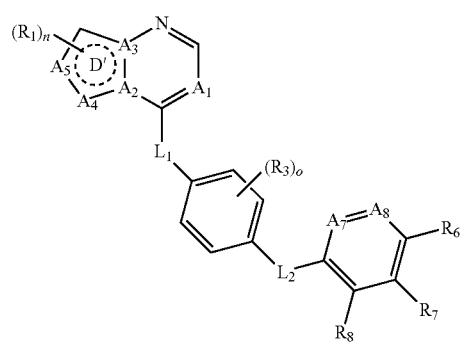

wherein $A^{1-5 \text{ and } 7-8}$, D', $L^1$, $L^2$, $R^1$, $R^3$, $R^{6-8}$, n and o are defined herein.

In another embodiment, the invention provides compounds of Formulas II, II-A, II-B and III, which are similar in structure to Formula I above. The invention also provides processes for making compounds of Formulas I-III, as well as intermediates useful in such processes.

The compounds provided by the invention have Aurora kinase modulatory activity and, in particular, inhibitory activity. To this end, the invention further provides the use of these compounds, as a free base or as a pharmaceutically acceptable salt form thereof, in the preparation and manufacture of a pharmaceutical composition (also referred to herein as "medicament") for therapeutic, prophylactic, acute or chronic treatment of cancer. Thus, the compounds of the invention are useful in the manufacture of anti-cancer medicaments and of medicaments to attenuate or prevent disorders through inhibition of Aurora kinase activity. For example, in one embodiment, the invention provides a pharmaceutical composition comprising a therapeutically-effective amount of a compound of Formula I, II, II-A, II-B or III in association with at least one pharmaceutically-acceptable excipient.

DETAILED DESCRIPTION OF THE INVENTION

In one embodiment of the invention, compounds useful for treating Aurora kinase and related disorders, including cancer and inflammation, are defined by Formula I:

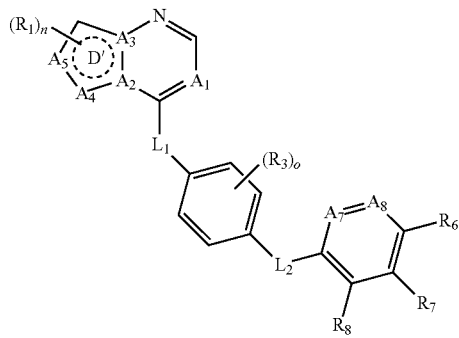

I or a stereoisomer, a tautomer, a solvate, a hydrate, or a pharmaceutically acceptable salt form thereof, wherein $A^1$ is N or $CR^2$;

D' is a fused heteroaryl ring wherein one of $A^2$ and $A^3$, independently, is N and the other of $A^2$ and $A^3$ is C, and each of $A^4$ and $A^5$, independently, is N or $CR^1$, provided that both of $A^4$ and $A^5$, independently, are not N;

each of $L^1$ and $L^2$, independently, is —O—, —$NR^4$—, —S—, —C(O)—, —S(O)—, —$SO_2$— or —$CR^4R^4$—, wherein each $R^4$, independently, is H, halo, OH, $C_{1-6}$alkoxyl, NH—$C_{1-6}$alkyl, CN or $C_{1-6}$alkyl;

each of $A^7$ and $A^8$, independently, is N or $CR^5$, provided at least one of $A^7$ and $A^8$ is N;

each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —OC(O)$NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

$R^2$ is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

$R^5$ is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

each of $R^6$, $R^7$ and $R^8$, independently, is $R^9$;

alternatively, either of $R^6$ or $R^8$, independently, taken together with $R^7$ and the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^9$;

each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, $COOR^{10}$, $C(O)NR^4R^{10}$, $NR^4C(O)R^{10}$, $NR^4C(O)NR^4R^{10}$, $NR^4(COOR^{10})$, $S(O)_2R^{10}$, $S(O)_2NR^4R^{10}$, $NR^4S(O)_2R^{10}$, $NR^4S(O)_2NR^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

n is 0, 1 or 2; and o is 0, 1 or 2, provided the compound is not 4-phenyl-N-(4-(pyrazolo[1,5-a]pyrimidin-7-yl-oxy)phenyl)phthalazin-1-amine.

It is worthy of note that the instant invention does not include the compound of 4-phenyl-N-(4-(pyrazolo[1,5-a]pyrimidin-7-yl-oxy)phenyl)phthalazin-1-amine, or pharmaceutically acceptable salts thereof.

In another embodiment, Formula I includes compounds wherein $A^1$ is N or $CR^2$;

$L^1$ is —O—, —S— or —$NR^4$—;

$L^2$ is —$NR^4$—; and

R[6] is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and $R^7$ and $R^8$, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^9$, in conjunction with any of the above or below embodiments.

In another embodiment of the invention, compounds, and pharmaceutically acceptable salts thereof, useful for treating Aurora kinase and related disorders, including cancer and inflammation, are generally defined by Formula II:

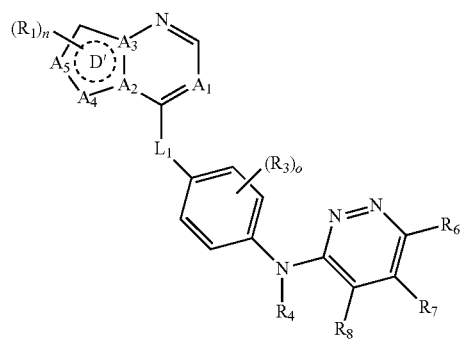

II wherein
when $A^1$ is N then D' is a fused heteroaryl ring wherein $A^2$ is C, $A^3$ is N and each of $A^4$ and $A^5$, independently, is $CR^1$ or
when $A^1$ is $CR^2$, then D' is a fused heteroaryl ring wherein $A^2$ is N, $A^3$ is C, $A^4$ is N and $A^5$ is $CR^1$;

$L^1$ is —O—, —S—, or —$NR^4$—;

each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

$R^2$ is H, halo, haloalkyl, haloalkoxyl, CN, OH, SH, $NO_2$, $NH_2$, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl or —$C(O)R^9$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

$R^4$ is H or $C_{1-6}$alkyl;

$R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

each of $R^7$ and $R^8$, independently, is $R^9$;

alternatively, $R^7$ and $R^8$, independently, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of $R^9$;

each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, $COOR^{10}$, $C(O)NR^4R^{10}$, $NR^4C(O)R^{10}$, $NR^4C(O)NR^4R^{10}$, $NR^4(COOR^{10})$, $S(O)_2R^{10}$, $S(O)_2NR^4R^{10}$, $NR^4S(O)_2R^{10}$, $NR^4S(O)_2NR^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

n is 0, 1, 2 or 3; and
o is 0, 1 or 2.

In another embodiment, the compounds of the present invention include compounds of Formula III:

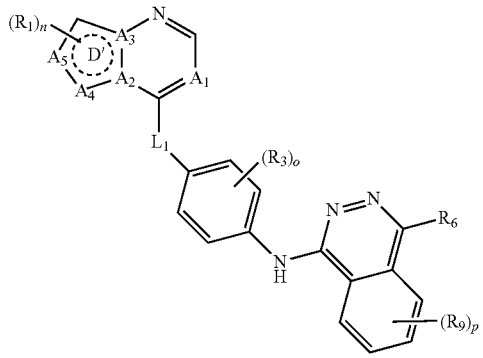

or a pharmaceutically acceptable salt thereof, wherein
$A^1$ is N or $CR^2$;

D' is a fused heteroaryl ring wherein one of $A^2$ and $A^3$, independently, is N and the other of $A^2$ and $A^3$ is C, and each of $A^4$ and $A^5$, independently, is N or $CR^1$, provided that both of $A^4$ and $A^5$, independently, are not N;

$L^1$ is —O—, —$NR^4$—, —S—, —C(O)—, —S(O)—, —$SO_2$— or —$CR^4R^4$—;

each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

$R^2$ is H, halo, haloalkyl, haloalkoxyl, CN, OH, SH, $NO_2$, $NH_2$, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl or —$C(O)R^9$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

$R^4$ is H or $C_{1-6}$alkyl;

$R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

each $R^9$, independently, is H, halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $SR^{10}$, $OR^{10}$, $NR^4R^{10}$, $C(O)R^{10}$, $COOR^{10}$, $C(O)NR^4R^{10}$, $NR^4C(O)R^{10}$, $NR^4C(O)NR^4R^{10}$, $NR^4(COOR^{10})$, $S(O)_2R^{10}$, $S(O)_2NR^4R^{10}$, $NR^4S(O)_2R^{10}$, $NR^4S(O)_2NR^4R^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

n is 0, 1, 2 or 3;
o is 0, 1 or 2; and
p is 0, 1 or 2.

Accordingly, the D' ring of Formulas I, II and III is a heteroaromatic ring comprising at least one and up to three (3) nitrogen atoms.

In another embodiment, the compounds of Formulas I, II and III include compounds wherein $A^1$ is N, in conjunction with any of the above or below embodiments.

In another embodiment, the compounds of Formulas I, II and III include compounds wherein $A^1$ is $CR^2$, in conjunction with any of the above or below embodiments.

In another embodiment, the compounds of Formulas I, II and III include compounds wherein $A^1$ is $CR^2$ wherein $R^2$ is either H or a halogen, in conjunction with any of the above or below embodiments.

In another embodiment, the compounds of Formulas I, II and III include compounds wherein D' is

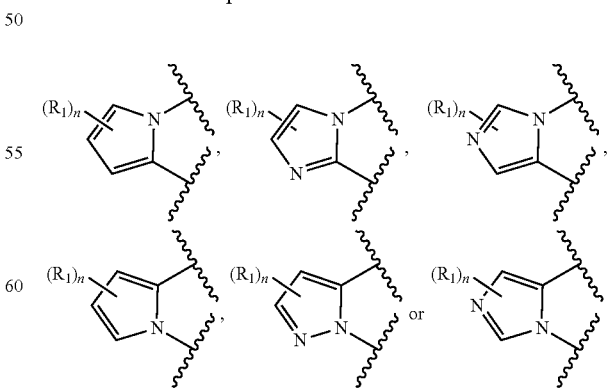

wherein $R^1$ and n are as defined in Formulas I, II and III above, in conjunction with any of the above or below embodiments.

In another embodiment, the compounds of Formulas I, II and III include compounds wherein D' is

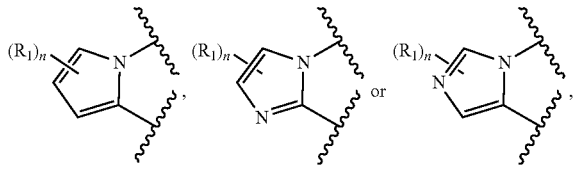

wherein $R^1$ and n are as defined in Formulas I, II and III, in conjunction with any of the above or below embodiments.

In another embodiment, the compounds of Formulas I, II and III include compounds wherein D' is

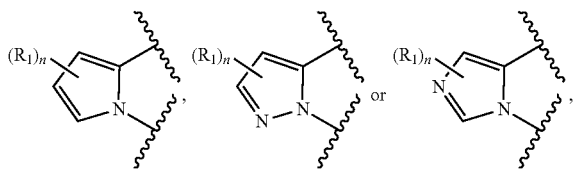

wherein $R^1$ and n are as defined in Formulas I, II and III, in conjunction with any of the above or below embodiments.

In another embodiment, the compounds of Formulas I, II and III include compounds wherein D' is

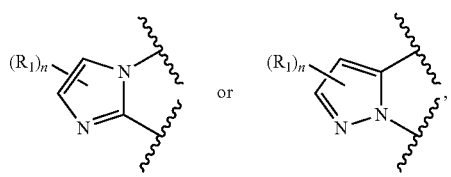

wherein $R^1$ and n are as defined in Formulas I, II and III, in conjunction with any of the above or below embodiments.

In another embodiment, the compounds of Formulas I, II and III include compounds wherein D' is

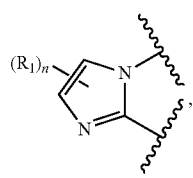

wherein $R^1$ and n are as defined in Formulas I, II and III, in conjunction with any of the above or below embodiments.

In another embodiment, the compounds of Formulas I, II and III include compounds wherein D' is

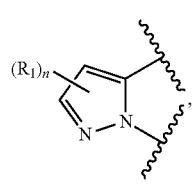

wherein $R^1$ and n are as defined in Formulas I, II and III, in conjunction with any of the above or below embodiments.

In another embodiment, the compounds of Formulas I, II and III include compounds wherein D' is

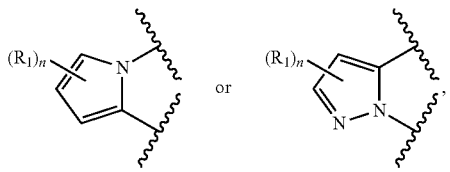

wherein $R^1$ and n are as defined in Formulas I, II and III, in conjunction with any of the above or below embodiments.

In another embodiment, Formulas I, II and III include compounds wherein when $A^1$ is N then D' is a fused heteroaryl ring wherein $A^2$ is C, $A^3$ is N and each of $A^4$ and $A^5$, independently, is $CR^1$ or when $A^1$ is $CR^2$, then D' is a fused heteroaryl ring wherein $A^2$ is N, $A^3$ is C, $A^4$ is N and $A^5$ is $CR^1$, in conjunction with any of the above or below embodiments.

In another embodiment, Formulas I, II and III include compounds wherein when $A^1$ is N then D' is a fused heteroaryl ring wherein $A^2$ is C, $A^3$ is N and each of $A^4$ and $A^5$, independently, is $CR^1$, in conjunction with any of the above or below embodiments.

In another embodiment, Formulas I, II and III include compounds wherein when $A^1$ is $CR^2$, then D' is a fused heteroaryl ring wherein $A^2$ is N, $A^3$ is C, $A^4$ is N and $A^5$ is $CR^1$, in conjunction with any of the above or below embodiments.

In another embodiment, Formula I includes compounds wherein of $A^7$ is N and $A^8$ is $CR^5$, in conjunction with any of the above or below embodiments.

In another embodiment, Formula I includes compounds wherein of $A^8$ is N and $A^7$ is $CR^5$, in conjunction with any of the above or below embodiments.

In another embodiment, Formula I includes compounds wherein each of $A^7$ and $A^8$ is N, in conjunction with any of the above or below embodiments.

In another embodiment, Formulas I, II and III include compounds wherein $L^1$ is —O—, in conjunction with any of the above or below embodiments.

In another embodiment, Formulas I, II and III include compounds wherein $L^1$ is —$NR^4$—, in conjunction with any of the above or below embodiments.

In another embodiment, Formulas I, II and III includes compounds wherein $L^1$ is —NH—, in conjunction with any of the above or below embodiments.

In another embodiment, Formulas I, II and III include compounds wherein $L^1$ is —S—, in conjunction with any of the above or below embodiments.

In another embodiment, Formulas I, II and III include compounds wherein $L^1$ is —C(O)—, in conjunction with any of the above or below embodiments.

In another embodiment, Formulas I, II and III include compounds wherein $L^1$ is —S(O)—, in conjunction with any of the above or below embodiments.

In another embodiment, Formulas I, II and III include compounds wherein $L^1$ is —$SO_2$—, in conjunction with any of the above or below embodiments.

In another embodiment, Formulas I, II and III include compounds wherein $L^1$ is —$CR^4R^4$—, in conjunction with any of the above or below embodiments.

In another embodiment, Formula I includes compounds wherein $L^2$ is —O—, in conjunction with any of the above or below embodiments.

In another embodiment, Formula I includes compounds wherein $L^2$ is —$NR^4$—, in conjunction with any of the above or below embodiments.

In another embodiment, Formula I includes compounds wherein $L^2$ is —NH—, in conjunction with any of the above or below embodiments.

In another embodiment, Formula I includes compounds wherein $L^2$ is —S—, in conjunction with any of the above or below embodiments.

In another embodiment, Formula I includes compounds wherein $L^2$ is —C(O)—, in conjunction with any of the above or below embodiments.

In another embodiment, Formula I includes compounds wherein $L^2$ is —S(O)—, in conjunction with any of the above or below embodiments.

In another embodiment, Formula I includes compounds wherein $L^2$ is —$SO_2$—, in conjunction with any of the above or below embodiments.

In another embodiment, Formula I includes compounds wherein $L^2$ is —$CR^4R^4$—, in conjunction with any of the above or below embodiments.

In another embodiment, Formulas I, II and III include compounds wherein $R^1$ is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$ or —$C(O)R^9$, in conjunction with any of the above or below embodiments.

In another embodiment, Formulas I, II and III include compounds wherein each $R^1$, independently, is $COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$ or —$NR^9S(O)_2R^9$, in conjunction with any of the above or below embodiments.

In another embodiment, Formulas I, II and III include compounds wherein each $R^1$, independently, is a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$, in conjunction with any of the above or below embodiments.

In another embodiment, Formulas I, II and III include compounds wherein each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$, or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$, in conjunction with any of the above or below embodiments.

In another embodiment, Formulas I, II and III include compounds wherein each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl is optionally substituted independently with 1-5 substituents of $R^9$, in conjunction with any of the above or below embodiments.

In another embodiment, Formulas I, II and III include compounds wherein each $R^1$, independently, is halo, haloalkyl, haloalkoxyl, CN, OH, SH, $NO_2$, $NH_2$, acetyl, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$, wherein each of the $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl is optionally substituted independently with 1-5 substituents of $R^9$, in conjunction with any of the above or below embodiments.

In another embodiment, Formulas I, II and III include compounds wherein each $R^1$, independently, is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$, in conjunction with any of the above or below embodiments.

In another embodiment, Formulas I, II and III include compounds wherein $R^2$ is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$, in conjunction with any of the above or below embodiments.

In another embodiment, Formulas I, II and III include compounds wherein $R^2$ is H, halo, haloalkyl, haloalkoxyl, CN, OH, SH, $NO_2$, $NH_2$, $C_{1-10}$-alkoxyl or $C_{1-10}$-alkyl, in conjunction with any of the above or below embodiments.

In another embodiment, Formulas I, II and III include compounds wherein $R^2$ is H, F, Cl, Br, I, $CF_3$, haloalkyl, CN, OH, SH, $NO_2$, $NH_2$, methyl, ethyl, propyl, methoxyl, ethoxyl, cyclopropyl or acetyl, in conjunction with any of the above or below embodiments.

In another embodiment, Formulas I, II and III include compounds wherein each $R^3$, independently, is H, halo, haloalkyl, haloalkoxyl, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$, in conjunction with any of the above or below embodiments.

In another embodiment, Formulas I, II and III include compounds wherein each $R^3$, independently, is H, halo, haloalkyl, haloalkoxyl, CN, OH, SH, NO$_2$, NH$_2$, C$_{1-10}$-alkoxyl or C$_{1-10}$-alkyl, in conjunction with any of the above or below embodiments.

In another embodiment, Formulas I, II and III include compounds wherein each R$^3$, independently, is H, F, Cl, Br, I, CF$_3$, haloalkyl, CN, OH, SH, NO$_2$, NH$_2$, methyl, ethyl, propyl, methoxyl, ethoxyl, cyclopropyl or acetyl, in conjunction with any of the above or below embodiments.

In another embodiment, Formulas I, II and III include compounds wherein each R$^3$, independently, is H, F, Cl, Br, CF$_3$, haloalkyl, CN, OH, SH, NO$_2$, NH$_2$, methyl, ethyl, methoxyl, ethoxyl, cyclopropyl, aminomethyl or acetyl, in conjunction with any of the above or below embodiments.

In another embodiment, Formulas I, II and III include compounds wherein each R$^4$, independently, is H, CN, NO$_2$, NH$_2$, acetyl or C$_{1-6}$-alkyl, in conjunction with any of the above or below embodiments.

In another embodiment, Formulas I, II and III include compounds wherein each R$^4$, independently, is H or C$_{1-6}$-alkyl, in conjunction with any of the above or below embodiments.

In another embodiment, Formulas I, II and III include compounds wherein each R$^4$, independently, is H or methyl, in conjunction with any of the above or below embodiments.

In another embodiment, Formulas I, II and III include compounds wherein each R$^4$, independently, is H, in conjunction with any of the above or below embodiments.

In another embodiment, Formulas I, II and III include compounds wherein R$^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl, in conjunction with any of the above or below embodiments.

In another embodiment, Formulas I, II and III include compounds wherein R$^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl, in conjunction with any of the above or below embodiments.

In another embodiment, Formulas I, II and III include compounds wherein R$^6$ is phenyl, pyridyl, pyrimidinyl, pyridazinyl, pyazinyl, triazinyl, thiophenyl, furyl, tetrahydrofuranyl, pyrrolyl, pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, cyclopentyl, cyclohexyl or pyranyl, each of which is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl, in conjunction with any of the above or below embodiments.

In another embodiment, Formulas I, II and III include compounds wherein R$^6$ is phenyl, pyridyl, pyrimidinyl, pyridazinyl, pyazinyl, thiophenyl, furyl, pyrrolyl, pyrazolyl, imidazolyl, triazolyl, tetrazolyl, thiazolyl, thiadiazolyl, oxazolyl, oxadiazolyl, isoxazolyl, isothiazolyl, dioxozinyl, 2,3-dihydro-1,4-benzoxazinyl, 1,3-benzodioxolyl, hexahydropyrrolo[1,2-a]pyrazinyl, cyclopropyl or cyclobutyl, each of which is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-benzyl or phenyl, in conjunction with any of the above or below embodiments.

In another embodiment, Formulas I and II include compounds wherein each of R$^7$ and R$^8$ independently, is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, SR$^{10}$, OR$^{10}$, NR$^4$R$^{10}$, C(O)R$^{10}$, in conjunction with any of the above or below embodiments.

In another embodiment, Formulas I and II include compounds wherein either of R$^7$ or R$^8$, independently, is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl, in conjunction with any of the above or below embodiments.

In another embodiment, Formulas I and II include compounds wherein R$^8$ taken together with R$^7$ and the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of R$^9$, in conjunction with any of the above or below embodiments.

In another embodiment, Formulas I and II include compounds wherein R$^8$ taken together with R$^7$ and the carbon atoms to which they are attached form a phenyl ring optionally substituted independently with 1-4 substituents of R$^9$, in conjunction with any of the above or below embodiments.

In another embodiment, Formulas I and II include compounds wherein R$^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl; and R⁷ and R⁸, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of R⁹, in conjunction with any of the above or below embodiments.

In another embodiment, Formulas I and II include compounds wherein A¹ is N and D' is a fused heteroaryl ring wherein A² is C, A³ is N and each of A⁴ and A⁵, independently, is CR¹;

R⁶ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of R¹⁰, halo, haloalkyl, haloalkoxyl, CN, NO₂, NH₂, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and R⁷ and R⁸, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of R⁹, in conjunction with any of the above or below embodiments.

In another embodiment, Formulas I and II include compounds wherein A¹ is CR² and D' is a fused heteroaryl ring wherein A² is N, A³ is C, A⁴ is N and A⁵ is CR¹;

R⁶ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of R¹⁰, halo, haloalkyl, haloalkoxyl, CN, NO₂, NH₂, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl; and R⁷ and R⁸, taken together with the carbon atoms to which they are attached form a phenyl ring optionally substituted independently with 1-4 substituents of R⁹, in conjunction with any of the above or below embodiments.

In another embodiment, Formula III include compounds wherein

A¹ is N and D' is a fused heteroaryl ring wherein A² is C, A³ is N and each of A⁴ and A⁵, independently, is CR¹; and R⁶ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of R¹⁰, halo, haloalkyl, haloalkoxyl, CN, NO₂, NH₂, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In another embodiment, Formula III include compounds wherein

A¹ is CR² and D' is a fused heteroaryl ring wherein A² is N, A³ is C, A⁴ is N and A⁵ is CR¹; and R⁶ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of R¹⁰, halo, haloalkyl, haloalkoxyl, CN, NO₂, NH₂, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl, in conjunction with any of the above or below embodiments.

In yet another embodiment, the invention provides compounds generally defined by Formula IV-A:

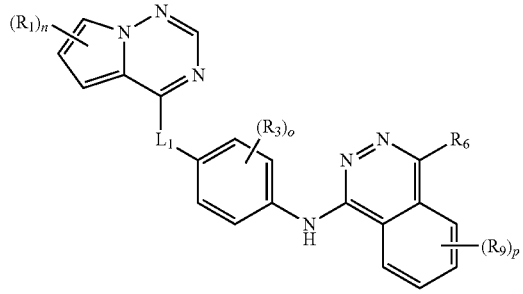

IV-A or stereoisomer, tautomer, solvate, pharmaceutically acceptable salt or prodrug thereof, wherein L¹ is —O—, —NR⁴—, —S— wherein R⁴ is H, halo, OH, $C_{1-6}$alkoxyl, NH—$C_{1-6}$alkyl, CN or $C_{1-6}$alkyl;

each R¹, independently, is halo, haloalkyl, haloalkoxyl, oxo, CN, OH, SH, NO₂, NH₂, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

$R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^9$, benzyl or phenyl;

each $R^9$, independently, is halo, haloalkyl, haloalkoxyl, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-10}$-alkyl, $COOC_{1-10}$-alkyl, $C(O)NR^4C_{1-10}$-alkyl, $NR^4C(O)C_{1-10}$-alkyl;

n is 0, 1, 2 or 3;

o is 0, 1 or 2; and p is 0, 1 or 2.

In yet another embodiment, the invention provides compounds generally defined by Formula IV-B:

IV-B

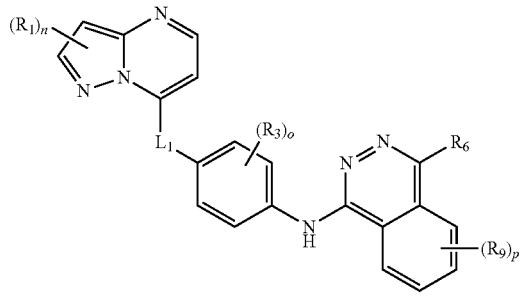

or stereoisomer, tautomer, solvate, pharmaceutically acceptable salt or prodrug thereof, wherein $L^1$ is —O—, —$NR^4$—, —S— wherein $R^4$ is H, halo, OH, $C_{1-6}$alkoxyl, NH—$C_{1-6}$alkyl, CN or $C_{1-6}$alkyl;

each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;

each $R^3$, independently, is H, halo, haloalkyl, haloalkoxyl, oxo, CN, OH, SH, $NO_2$, $NH_2$, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or —$C(O)R^9$;

$R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^9$, benzyl or phenyl;

each $R^9$, independently, is halo, haloalkyl, haloalkoxyl, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, $C(O)C_{1-10}$-alkyl, $COOC_{1-10}$-alkyl, $C(O)NR^4C_{1-10}$-alkyl, $NR^4C(O)C_{1-10}$-alkyl;

n is 0, 1, 2 or 3;

o is 0, 1 or 2; and p is 0, 1 or 2.

The many different embodiments for various elements, chemical moieties or R or L groups described and defined hereinabove with respect to compounds of Formula I may also apply to compounds of Formula II, III and IV-A and IV-B where appropriate, as appreciated by those of ordinary skill in the art.

In yet another embodiment, Formulas I, II, III and IV-A and IV-B include the exemplary compounds and derivatives, prodrugs, solvates, tautomers and pharmaceutically acceptable salt forms thereof, intermediates related thereto, examples of which are described in the Examples herein. In one embodiment, the invention provides the following compounds, and pharmaceutically acceptable salt forms thereof, selected from 4-(5-chloro-2-pyridinyl)-N-(4-(pyrazolo[1,5-a]pyrimidin-7-ylthio)phenyl)-1-phthalazinamine;

4-(5-methyl-2-pyridinyl)-N-(4-(pyrazolo[1,5-a]pyrimidin-7-ylthio)phenyl)-1-phthalazinamine;

4-(4-chlorophenyl)-N-(4((2-cyclopropylpyrazolo[1,5-a]pyrimidin-7-yl)thio)phenyl)-1-phthalazinamine;

N-(4-((2-cyclopropylpyrazolo[1,5-a]pyrimidin-7-yl)thio)phenyl)-4-phenyl-1-phthalazinamine;

N-(4-((2-cyclopropylpyrazolo[1,5-a]pyrimidin-7-yl)thio)phenyl)-4-(4-methyl-2-thienyl)-1-phthalazinamine;

4-(4-chlorophenyl)-N-(4-(pyrrolo[1,2-b]pyridazin-4-yloxy)phenyl)-1-phthalazinamine;

4-(4-chlorophenyl)-N-(4-(pyrrolo[2,1-f][1,2,4]triazin-4-yloxy)phenyl)-1-phthalazinamine;

4-(4-methyl-2-thienyl)-N-(4-(pyrrolo[2,1-f][1,2,4]triazin-4-yloxy)phenyl)-1-phthalazinamine;

4-(4-chlorophenyl)-N-(4-(pyrrolo[2,1-f][1,2,4]triazin-4-ylthio)phenyl)-1-phthalazinamine;

4-(4-methyl-2-thienyl)-N-(4-(pyrrolo[2,1-f][1,2,4]triazin-4-ylthio)phenyl)-1-phthalazinamine;

4-(4-chlorophenyl)-N-(4-((2-(2-propen-1-yloxy)pyrazolo[1,5-a]pyrimidin-7-yl)sulfanyl)phenyl)-1-phthalazinamine;

N-(4-((2-((2-(methyloxy)ethyl)oxy)pyrazolo[1,5-a]pyrimidin-7-yl)thio)phenyl)-4-phenyl-1-phthalazinamine;

N-(4-((2-((2-(methyloxy)ethyl)oxy)pyrazolo[1,5-a]pyrimidin-7-yl)thio)phenyl)-4-(4-methyl-2-thienyl)-1-phthalazinamine;

4-(4-chlorophenyl)-N-(4-((2-((2-(methyloxy)ethyl)oxy)pyrazolo[1,5-a]pyrimidin-7-yl)thio)phenyl)-1-phthalazinamine;

7-((4-((4-(4-chlorophenyl)-1-phthalazinyl)amino)phenyl)thio)pyrazolo[1,5-a]pyrimidin-2-ol;

N-(4-((5-chloropyrrolo[2,1-f][1,2,4]triazin-4-yl)thio)phenyl)-4-phenyl-1-phthalazinamine; and 4-(4-chlorophenyl)-N-(4((5-chloropyrrolo[2,1-f][1,2,4]triazin-4-yl)thio)phenyl)-1-phthalazinamine.

DEFINITIONS

The following definitions should further assist in understanding the scope of the invention described herein.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels of Aurora kinase(s) in the mammal.

The terms "treat", "treating" and "treatment" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The term "mammal" as used herein refers to any mammal classified as a mammal, including humans, cows, horses, dogs and cats. In one embodiment of the invention, the mammal is a human.

A "pharmaceutically-acceptable derivative" denotes any salt (also referred to as "pharmaceutically-acceptable salt"), any prodrug such as a phosphate or an ester of a compound of this invention, or any other compound which upon administration to a patient is capable of providing (directly or indirectly) a compound of this invention, or a metabolite or residue thereof, characterized by the ability to inhibit Aurora kinase.

The phrase "therapeutically-effective" is intended to quantify the amount of each agent, which will achieve the goal of improvement in disorder severity and the frequency of incidence over treatment of each agent by itself, while avoiding adverse side effects typically associated with alternative therapies.

The terms "ring" and "ring system" refer to a one or more rings, typically fused together where more than one ring, comprising the delineated number of atoms, said atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is not fully unsaturated.

"Leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals preferably having alpha to beta number of carbon atoms. For example a $C_1$-$C_{10}$ alkyl is an alkyl comprising 1 to 10 carbon atoms. Examples of such radicals include methyl, ethyl, n-propyl, isopropyl, n-butyl, isobutyl, sec-butyl, tert-butyl, pentyl, isoamyl, hexyl and the like. It is contemplated herein that alkyl radicals may be optionally substituted with various substituents, where indicated.

The term "alkenyl", alone or in combination, embraces linear or branched radicals having at least one carbon-carbon double bond and having two or more carbon atoms. Examples of alkenyl radicals include, without limitation, ethenyl, propenyl, allyl, propenyl, butenyl and 4-methylbutenyl. The term "alkenyl" embrace radicals having "cis" and "trans" orientations, or alternatively, "E" and "Z" orientations, as appreciated by those of ordinary skill in the art. It is contemplated herein that alkenyl radicals may be optionally substituted with various substituents, where indicated.

The term "alkynyl", alone or in combination, denotes linear or branched radicals having at least one carbon-carbon triple bond and having two or more carbon atoms. Examples of alkynyl radicals include, without limitation, ethynyl, propynyl (propargyl), butynyl, and the like. It is contemplated herein that alkynyl radicals may be optionally substituted with various substituents, where indicated.

The term "halo", alone or in combination, means halogens such as fluorine, chlorine, bromine or iodine atoms.

The term "haloalkyl", alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl dichloropropyl. "Perfluoroalkyl", as used herein, refers to alkyl radicals having all hydrogen atoms replaced with fluoro atoms. Examples include trifluoromethyl and pentafluoroethyl.

The term "hydroxyalkyl", alone or in combination, embraces linear or branched alkyl radicals having one or more carbon atoms any one of which may be substituted with one or more hydroxyl radicals. Examples of such radicals include hydroxymethyl, hydroxyethyl, hydroxypropyl, hydroxybutyl and hydroxyhexyl.

The term "alkoxy", alone or in combination, embraces linear or branched oxy-containing radicals each having alkyl portions of alpha to beta number of carbon atoms. For example, a $C_{1-10}$ alkoxy radical indicates an alkoxide having one to ten carbon atoms, arranged in a linear or branched fashion, attached to an oxygen atom. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "partially or fully saturated" as used herein, refers to a moiety, linear, branched or cyclic in nature, having no atom-atom double or triple bonds (fully saturated) or having one or more atom-atom double or triple bonds which are arranged such that where the structural moiety is cyclic, the cycle is not fully unsaturated (non-aromatic), as appreciated by those skilled in the art.

The term "fully unsaturated" as used herein, refers to a moiety having double or triple bonds, arranged in a manner such that the structure is aromatic in nature, as appreciated by those skilled in the art.

The term "aryl", alone or in combination, means a carbocyclic aromatic moiety containing one, two or even three rings wherein such rings may be attached together in a fused manner. Thus the term "aryl" embraces aromatic radicals such as phenyl, naphthyl, indenyl, tetrahydronaphthyl, anthracenyl, and indanyl. Said "aryl" group may have 1 or more substituents such as lower alkyl, hydroxyl, halo, haloalkyl, nitro, cyano, alkoxy and lower alkylamino, and the like. Phenyl substituted with —O—$CH_2$—O— forms an aryl benzodioxolyl substituent. Aryl as used herein, implies a fully unsaturated ring.

The term "heterocycles" or "heterocyclic radicals", alone or in combination, embraces saturated, partially saturated and partially unsaturated heteroatom-containing ring radicals, where the heteroatoms may be selected from nitrogen, sulfur and oxygen. This term does not include rings containing —O—O—, —O—S— or —S—S— portions. Said "heterocycle" may have 1 or more substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated (or partially unsaturated) heterocyclyl radicals include dihydrothienyl, dihydropyranyl, dihydrofuryl and dihydrothiazolyl.

The term "heteroaryl" radicals, alone or in combination, embraces fully unsaturated heteroatom-containing ring radicals, where the heteroatoms may be selected from nitrogen, sulfur and oxygen. Examples of heteroaryl radicals include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The terms "heterocycle" and "heteroaryl" also embraces radicals which are fused/condensed with aryl radicals: unsaturated condensed heterocyclic or heteroaryl groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals. Further examples of heteroaryl radicals include quinolyl, isoquinolyl, imidazolyl, pyridyl, thienyl, thiazolyl, oxazolyl, furyl, and pyrazinyl. Other examples of heteroaryl radicals are 5- or 6-membered heteroaryl, containing one or two heteroatoms selected from sulfur, nitrogen and oxygen, such as thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl radicals.

Examples of non-nitrogen containing heteroaryl include, without limitation, pyranyl, 2-furyl, 3-furyl, 2-thienyl, 3-thienyl, benzofuryl, benzothienyl, and the like.

Examples of partially and fully saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1$\lambda$'-benzo[d]isothiazol-6-yl, dihydropyranyl, dihydrofuryl and dihydrothiazolyl, and the like.

The term "sulfonyl", whether used alone or linked to other terms such as alkylsulfonyl, denotes respectively divalent radicals —$SO_2$—.

The term "carbonyl", whether used alone or with other terms, such as "aminocarbonyl", denotes —(C═O)—.

The term "$C_{1-10}$alkylthio" embraces radicals containing a linear or branched alkyl radical, of one to ten carbon atoms, attached to a divalent sulfur atom. An example of "alkylthio" is methylthio, ($CH_3S$—).

The term "aminoalkyl" and "diaminoalkyl" embraces "N—$C_{1-10}$alkylamino" and "N,N—$C_{1-10}$dialkylamino", respectively, where amino groups are independently substituted with one alkyl radical and with two alkyl radicals, respectively. Examples of alkylamino radicals include "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like.

The term "cycloalkyl" includes saturated carbocyclic groups. Examples of cycloalkyl groups include $C_3$-$C_6$ rings, such as compounds including, cyclopentyl, cyclopropyl, and cyclohexyl.

The term "cycloalkenyl" includes carbocyclic groups having one or more carbon-carbon double bonds including "cycloalkyldienyl" compounds. Examples of cycloalkenyl groups include $C_3$-$C_6$ rings, such as compounds including, without limitation, cyclopentenyl, cyclopentadienyl, cyclohexenyl and cycloheptadienyl.

The term "comprising" is meant to be open ended, including the indicated component(s) but not excluding other elements.

The terms "Formula I", "Formula II", "Formula III" and "Formula IV" include any sub formulas. For example "Formula IV" includes both Formulas IV-A and IV-B.

The present invention comprises processes for the preparation of a compound of Formulae I, II, III and IV.

Also included in the family of compounds of Formulas I-IV are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formulas I-IV may be prepared from an inorganic acid or from an organic acid. Examples of such inorganic acids include, without limitation, hydrochloric, hydrobromic, hydroiodic, nitric, carbonic, sulfuric and phosphoric acid. Examples of organic acids include, without limitation, aliphatic, cycloaliphatic, aromatic, arylaliphatic, heterocyclic, carboxylic and sulfonic classes of organic acids, examples of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid.

Suitable pharmaceutically-acceptable base addition salts of compounds of Formulas I-IV include, without limitation, metallic salts such as salts made from aluminum, calcium, lithium, magnesium, potassium, sodium and zinc, or salts made from organic bases including primary, secondary, tertiary amines and substituted amines including cyclic amines such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of the salts contemplated herein may be prepared by conventional means from the corresponding compound by reacting, for example, the appropriate acid or base with the compound of Formulas I-IV. When a basic group and an acid group are present in the same molecule, a compound of Formulas I-IV may also form internal salts.

General Synthetic Procedures

The compounds of the invention can be synthesized according to the following procedures of Schemes 1-8, wherein the substituents are as defined for Formulas I-IV, above, except where further noted. The synthetic methods described below are merely exemplary, and the compounds of the invention may be synthesized by alternate routes as appreciated by persons of ordinary skill in the art.

The following list of abbreviations used throughout the specification represent the following:

| | |
|---|---|
| ACN, AcCN, MeCN | acetonitrile |
| BSA | bovine serum albumin |
| $Cs_2CO_3$ | cesium carbonate |
| $CHCl_3$ | chloroform |
| $CH_2Cl_2$, DCM | dichloromethane, methylene chloride |
| DIBAL | diisobutylaluminum hydride |
| DIEA,(iPr$_2$Net) | diisopropylethylamine |
| DME | dimethoxyethane |
| DMF | dimethylformamide |
| DMAP | 4-dimethylaminopyridine |
| DMSO | dimethylsulfoxide |
| dppa | diphenylphosphoryl azide |
| EDC | 1-(3-dimethylaminopropyl)-3-ethylcarbodiimide hydrochloride |
| $Et_2O$ | diethyl ether |
| EtOAc | ethyl acetate |
| FBS | fetal bovine serum |
| g, gm | gram |
| h, hr | hour |
| HBr | hydrobromic acid |
| HCl | hydrochloric acid |
| HOBt | 1-hydroxybenzotriazole hydrate |
| $H_2$ | hydrogen |
| $H_2O_2$ | hydrogen peroxide |
| HATU | O-(7-azabenzotriazol-1-yl)-N,N,N',N'-tetramethyluroniumhexafluorophasphate |
| HPLC | high pressure liquid chromatagraphy |
| IPA, IpOH | isopropyl alcohol |
| $K_2CO_3$ | potassium carbonate |
| MCPBA | meta-chloroperbenzoic acid |
| $MgSO_4$ | magnesium sulfate |
| MeOH | methanol |
| $N_2$ | nitrogen |
| $NaHCO_3$ | sodium bicarbonate |
| NaOH | sodium hydroxide |
| NaH | sodium hydride |
| $Na_2SO_4$ | sodium sulfate |
| $NH_4Cl$ | ammonium chloride |
| $NH_4OH$ | ammonium chloride |
| NMP | N-methylpyrrolidinone |
| P(t -bu)$_3$ | tri(tert-butyl)phosphine |
| PBS | phospate buffered saline |
| Pd/C | palladium on carbon |
| Pd(PPh$_3$)$_4$ | palladium(0)triphenylphosphine tetrakis |
| Pd(PhCN)$_2$Cl$_2$ | palladium di-cyanophenyl dichloride |
| Pd(OAc)$_2$ | palladium acetate |
| Pd$_2$(dba)$_3$ | bis(dibenzylideneacetone) palladium |
| PyBop | benzotriazol-1-yl-oxy-tripyrrolidino-phosphonium hexafluorophosphate |

-continued

| | |
|---|---|
| RT, rt | room temperature |
| RBF | round bottom flask |
| rac-BINAP | 2,2'-Bis(diphenylphosphine)-1,1'-binaphthyl |
| TBTU | O-benzotriazol-1-yl-N,N,N',N'-tetramethyluronium tetrafluoroborate |
| TEA, Et$_3$N | triethylamine |
| TFA | trifluoroacetic acid |
| THF | tetrahydrofuran |

Scheme 1 (Method A)

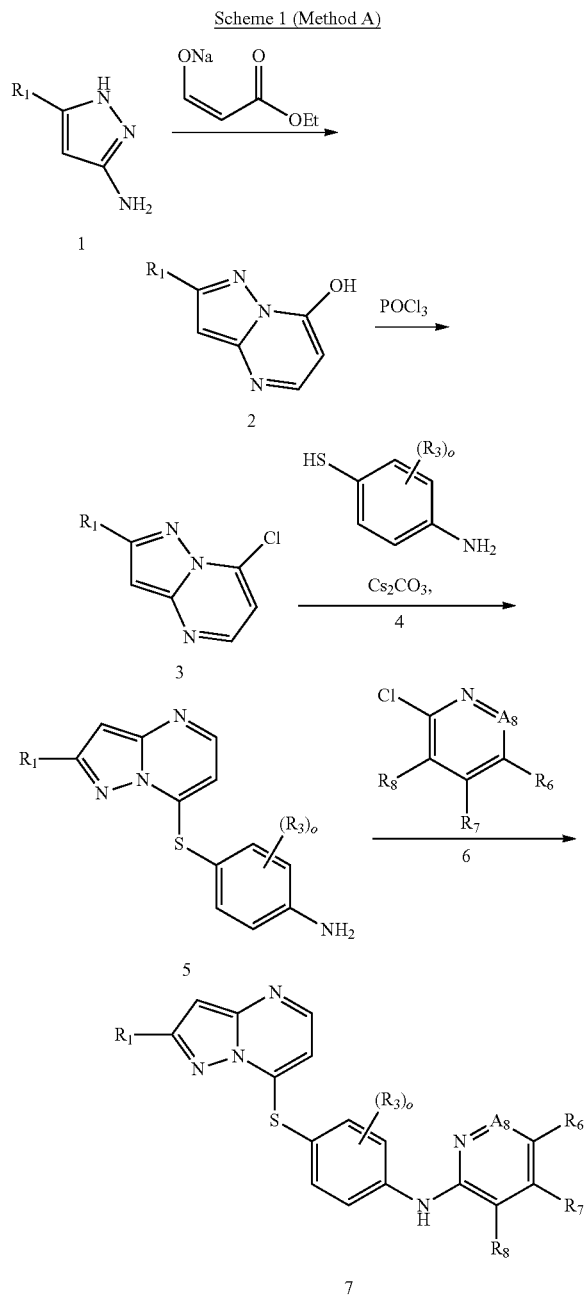

Compounds 7 of Formula I-IV (wherein L1 is S and L2 is NH), can be prepared according to the method generally described in Scheme 1. As shown, a base assisted reaction of hydroxyethylacrylate with an amino-pyrazole 1 affords the hydroxyl-pyrazolo pyrimidine 2 (where A1 is CH, A3 is C, A2 and A4 are each N and A5 is CR1, of the D' ring, are each CR1, respectively). The hydroxy group of compounds 2 may be functionalizaled or converted to a useable group, such as a chloride to form the corresponding chloride intermediate 3, under conventional, known methods, such as with phosphorus oxychloride (POCl3) as shown. Additional method(s) of preparing a chloro-pyrazolo-pyrimidine intermediate 3 (R1=H) is that described in Senga, K.; et al. J. Med. Chem. 1981, 24, 610-613.

The chloride of compound 3 can then be reacted with a suitably nucleophilic aniline species, such as a thiol 4 (wherein L$^1$ is a sulfur and L$^2$ is an NH; Note that phenols may also be used to prepare similar intermediates where L$^1$ is O), under basic conditions such as the use of a suitable case, including a cesium base as shown. The resulting intermediate 5 may then be reacted with a chloride material 6 under suitable conditions to afford the desired compounds 7.

The thiol 4 is generally sufficiently nucleophilic, under suitable conditions, to displace the chloride of compound 3. Compound 4 may also be an alcohol, a primary or secondary amine or a nucleophilic carbon species (all of which are not shown) to effect the transformation to compound 5, as appreciated by those skilled in the art. The amine group on compound 4 may be protected as necessary or left unprotected, as appreciated by those skilled in the art. Suitable bases to yield compound 5 include, without limitation, carbonate bases such as cesium carbonate (Cs$_2$CO$_3$), Na$_2$CO$_3$, K$_2$CO$_3$ and the like in a suitable solvent, whose properties will generally depend upon the solubility of the starting materials, polarity, and other factors readily appreciated in the art Amine 5, if protected may generally first be deprotected, and then reacted with an optionally substituted chloro-pyridine, chloro-pyridazine (where A$^8$ is N), chloro-phthalazine (where R$^7$ and R$^8$ taken together form a phenyl ring) and the like under suitable conditions, including without limitation, under basic conditions, acidic conditions and heated conditions, in suitable solvent or combination of solvents to afford compound 7, of Formulas I-IV. Representative examples of such reactions are further described hereinbelow.

Scheme 2 (Method B)

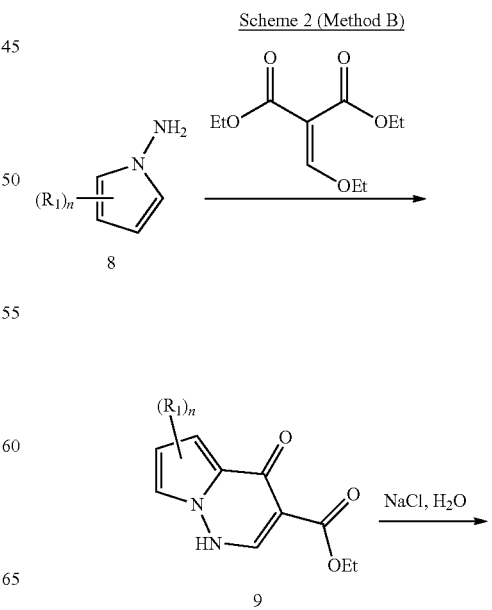

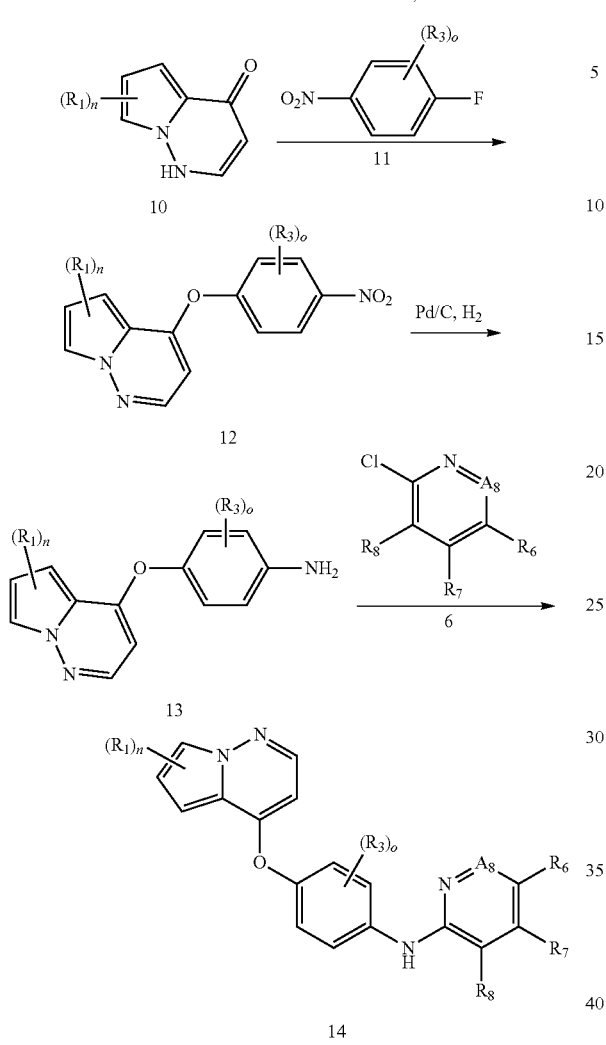

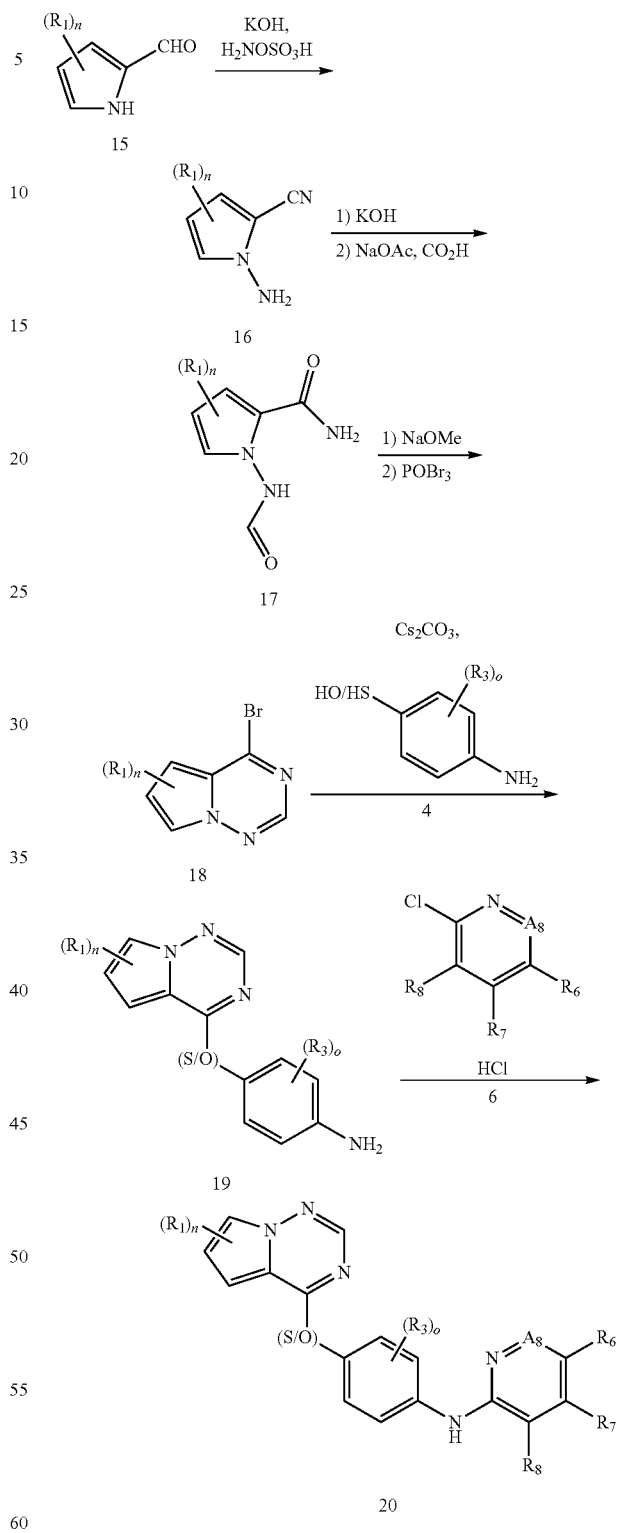

Compounds 14 of Formulas I-IV (where $L^1$ is O and $L^2$ is NH), can be prepared according to the method generally described in Scheme 2. As shown, diethyl 2-(ethoxymethylene) malonate can be reacted with an 1H-pyrrolo-amine 8 to afford the ring closed ethyl ester substituted-oxo-pyrrolopyridazine 9 (where $A^1$ is CH, $A^3$ is N, $A^2$ is C and $A^4$ and $A^5$, of the D' ring, are each $CR^1$, respectively). The ester group of compounds 9 may be hydrolyzed and decarboxylated, or otherwise eliminated, under conventional conditions, such as aqueous sodium chloride, to form the corresponding ketone intermediate 10, as shown. Arylation of compound 10 can be accomplished with a suitable base, such as DABCO, and the corresponding activated aryl group, such as fluoro-nitro-benzene 11, as shown. The nitro group of resulting intermediate 12 may first be reduced to the corresponding amino intermediate 13 under conventional conditions, such as hydrogenation un the presence of a suitable catalyst, as shown. The corresponding amine 13 can then be reacted with a chloride 6 under suitable conditions to afford the desired compounds 14.

Representative examples of such reactions are further described hereinbelow. Suitable transformation methods are known to those skilled in the art, and are generally described in Jerry March's Advanced Organic Chemistry, 4th edition (1992), which disclosure is hereby incorporated by reference in its entirety.

Compounds 20 of Formulas I-IV (where $L^1$ is S or O and $L^2$ is NH), can be prepared according to the method generally described in Scheme 3. As shown, the aldehyde group and amino group of carboxaldehyde-pyrrole 15, respectively, can be reacted with KOH and hydroxylamine-sulfonic acid to afford the corresponding cyano-1-amino pyrrole intermediate 16. The cyano and amino groups of compound 16 can be respectfully hydrolyzed and formylated by treatment with base followed by formic acid in the presence of sodium acetate to provide intermediate 17. The ring closure of intermediate 18 can be accomplished by reacting 17 with sodium methoxide. The bromide of compounds 18, obtained by bromination with phosphiorus oxybromide, may be reacted with a thiol or alcohol 4, under conventional conditions, to afford intermediate 19. The resulting aniline intermediate 19 may then be reacted with a heteroaryl chloride 6 under suitable conditions to afford the desired compounds 20.

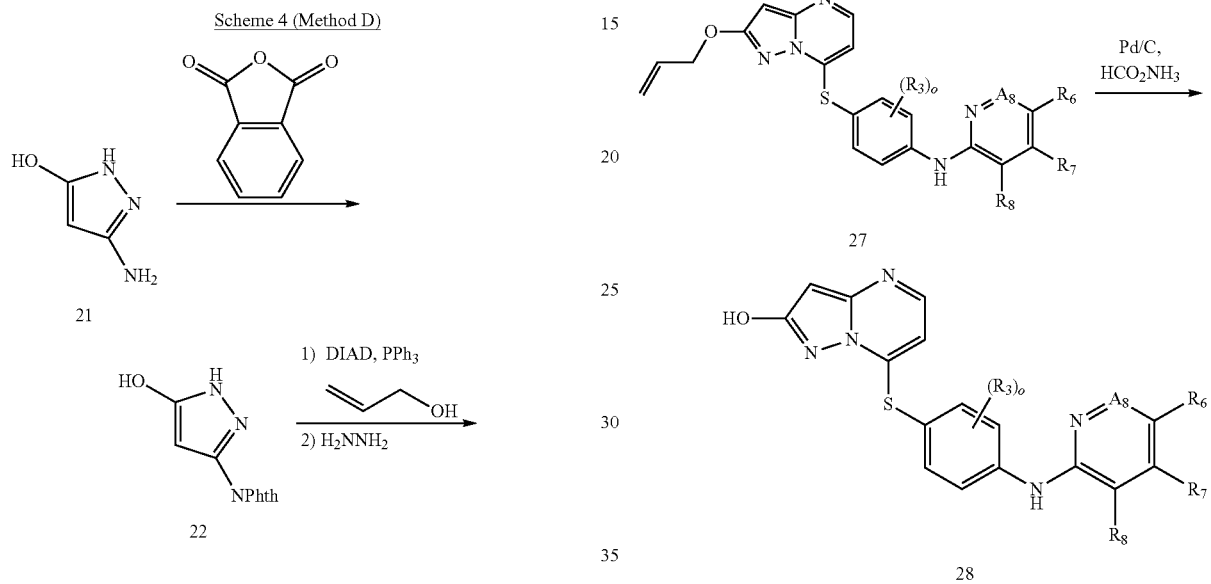

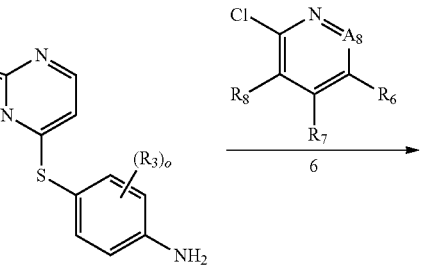

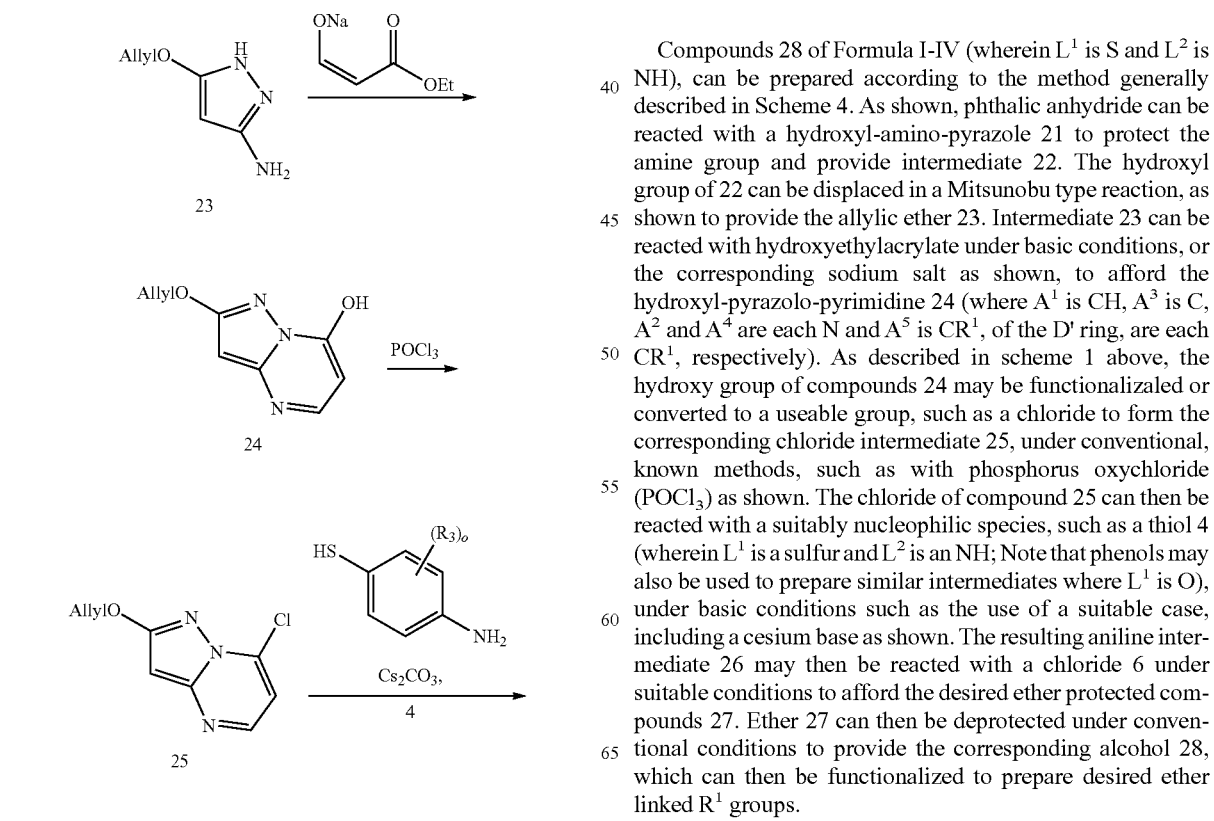

Compounds 28 of Formula I-IV (wherein $L^1$ is S and $L^2$ is NH), can be prepared according to the method generally described in Scheme 4. As shown, phthalic anhydride can be reacted with a hydroxyl-amino-pyrazole 21 to protect the amine group and provide intermediate 22. The hydroxyl group of 22 can be displaced in a Mitsunobu type reaction, as shown to provide the allylic ether 23. Intermediate 23 can be reacted with hydroxyethylacrylate under basic conditions, or the corresponding sodium salt as shown, to afford the hydroxyl-pyrazolo-pyrimidine 24 (where $A^1$ is CH, $A^3$ is C, $A^2$ and $A^4$ are each N and $A^5$ is $CR^1$, of the D' ring, are each $CR^1$, respectively). As described in scheme 1 above, the hydroxy group of compounds 24 may be functionalizaled or converted to a useable group, such as a chloride to form the corresponding chloride intermediate 25, under conventional, known methods, such as with phosphorus oxychloride ($POCl_3$) as shown. The chloride of compound 25 can then be reacted with a suitably nucleophilic species, such as a thiol 4 (wherein $L^1$ is a sulfur and $L^2$ is an NH; Note that phenols may also be used to prepare similar intermediates where $L^1$ is O), under basic conditions such as the use of a suitable case, including a cesium base as shown. The resulting aniline intermediate 26 may then be reacted with a chloride 6 under suitable conditions to afford the desired ether protected compounds 27. Ether 27 can then be deprotected under conventional conditions to provide the corresponding alcohol 28, which can then be functionalized to prepare desired ether linked $R^1$ groups.

Scheme 5 (Method E)

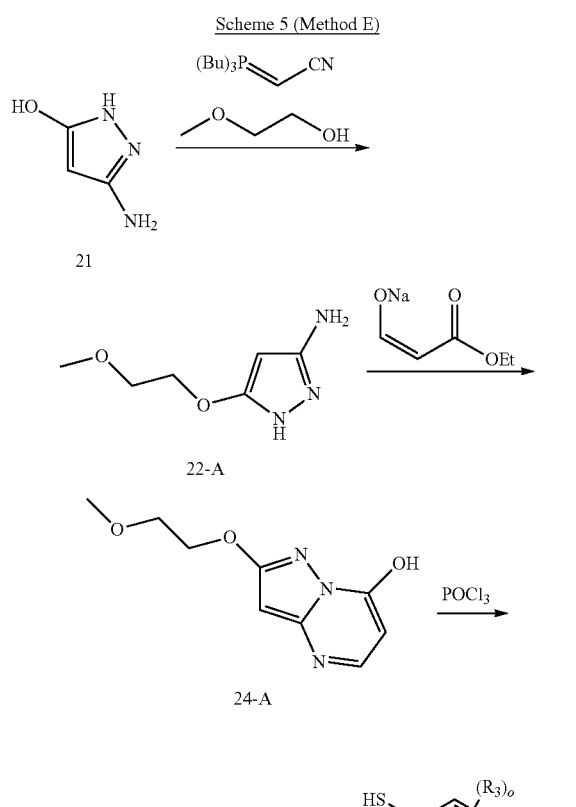

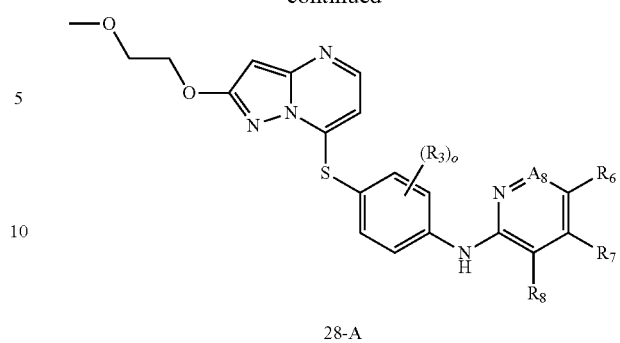

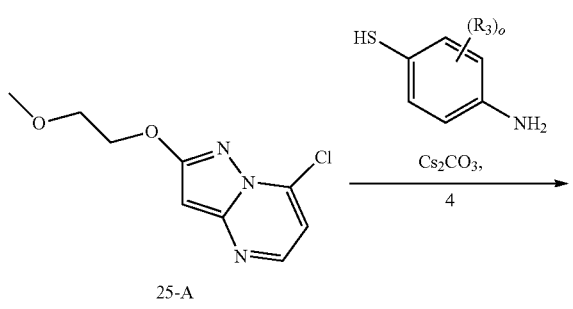

Compounds 28A of Formula I-IV (wherein $L^1$ is S and $L^2$ is NH), can be prepared according to the method generally described in Scheme 5. As shown, 2-hydroxylethyl-methyl ether can be reacted with a hydroxyl-amino-pyrazole 21-A to functionalize the hydroxyl group and provide intermediate 22-A. Intermediate 22-A can be reacted with hydroxyethylacrylate under basic conditions, or the corresponding sodium salt as shown, to afford the hydroxyl-pyrazolo-pyrimidine 24-A (where $A^1$ is CH, $A^3$ is C, $A^2$ and $A^4$ are each N and $A^5$ is $CR^1$, of the D' ring, are each $CR^1$, respectively). As described in scheme 1 above, the hydroxy group of compounds 24-A may be functionalizaled or converted to a useable group, such as a chloride to form the corresponding chloride intermediate 25-A, under conventional, known methods, such as with phosphorus oxychloride ($POCl_3$) as shown. The chloride of compound 25-A can then be reacted with a suitably nucleophilic species, such as a thiol 4 (wherein $L^1$ is a sulfur and $L^2$ is an NH; Note that phenols may also be used to prepare similar intermediates where $L^1$ is O), under basic conditions such as the use of a suitable case, including a cesium base as shown. The resulting aniline intermediate 26-A may then be reacted with a chloride 6 under suitable conditions to afford the desired ether compounds 27-A.

Scheme 6 (Method F)

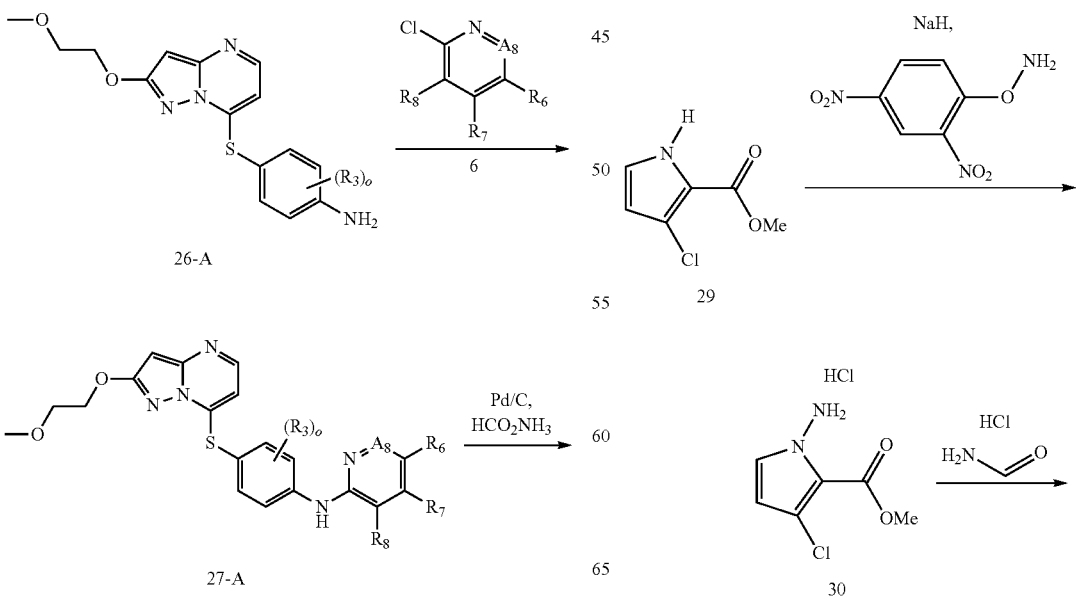

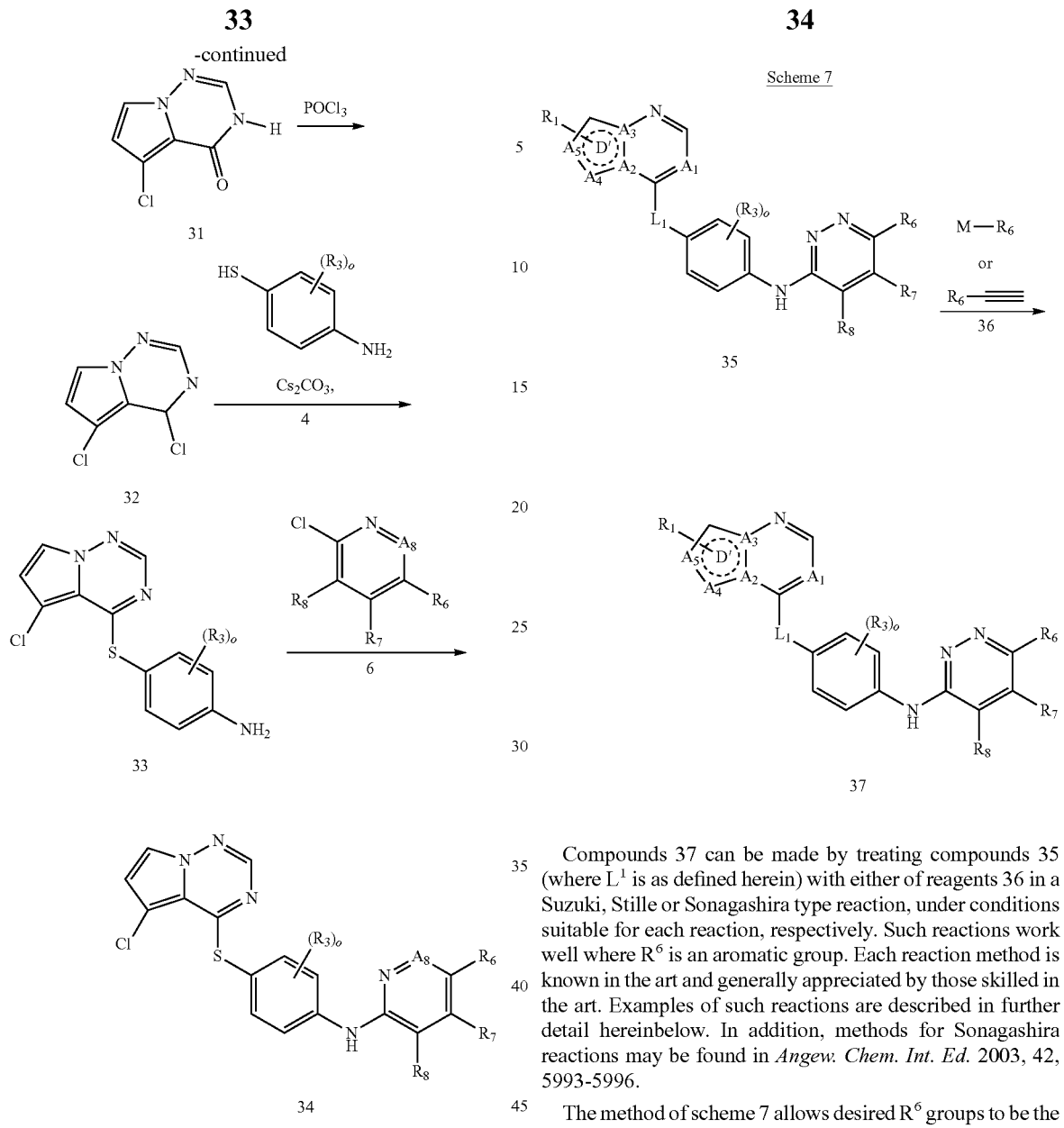

Compounds 34 of Formula I-IV (wherein $L^1$ is S and $L^2$ is NH), can be prepared according to the method generally described in Scheme 6. As shown, methyl-chloro-pyrrole carboxylate 29 can be reacted with dinitrophenylhydroxylamine in the presence of a strong base, such as sodium hydride in a suitable solvent, to afford aminopyrrole 30. Amino-pyrrole 30 can be reacted with formamide (can be used here as a solvent as well) to effect ring closure and provide intermediate 31. Compound 31 can be converted to the corresponding chloride 32 under conventional conditions, such as $POCl_3$ shown in scheme 1. Further, and as shown in scheme 1, chloride 32 may be reacted with and displaced by a suitable thiol 4, as shown, to provide coupled adduct 33. The resulting aniline intermediate 33 may then be reacted with a chloride 6 under suitable conditions to afford the desired compounds 34. Chloride 34 can then be reacted under conventional conditions with suitable nucleophilic species to provide the corresponding desired $R^1$ substituted pyrrolo-triazines (not shown).

Compounds 37 can be made by treating compounds 35 (where $L^1$ is as defined herein) with either of reagents 36 in a Suzuki, Stille or Sonagashira type reaction, under conditions suitable for each reaction, respectively. Such reactions work well where $R^6$ is an aromatic group. Each reaction method is known in the art and generally appreciated by those skilled in the art. Examples of such reactions are described in further detail hereinbelow. In addition, methods for Sonagashira reactions may be found in *Angew. Chem. Int. Ed.* 2003, 42, 5993-5996.

The method of scheme 7 allows desired $R^6$ groups to be the final step of synthesis of compounds 37. Care must be taken to restrict the $R^1$, $R^7$ and $R^8$ in this method to those groups, which would not interfere with or react under suitable reaction method and/or conditions to form compounds 37, as appreciated by persons of ordinary skill in the art.

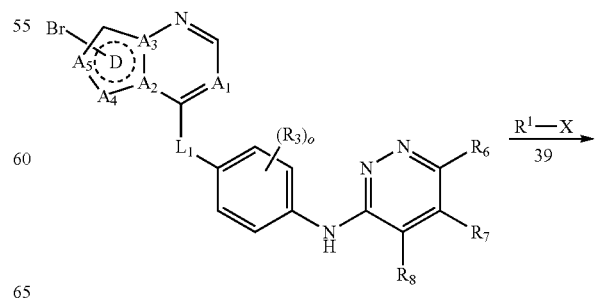

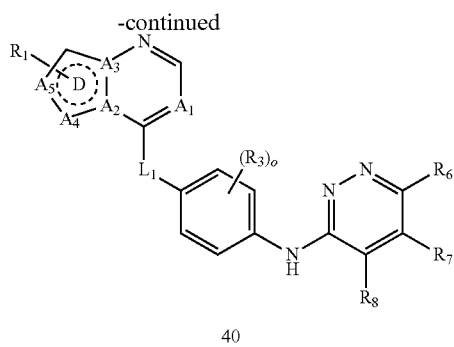

Compounds 40 may be prepared by a single reaction between a bromo-substituted compound 38 and a desired R[1] group appropriately substituted with a nucleophile or other suitable group to prepare compound 40. Such transformations may be accomplished using a variety of different methods, as appreciated by those skilled in the art. For example, desirable amino-R[1] groups can be installed at a suitable position on a D' ring by treating bromide 38 in the presence of a suitable palladium species and a suitable R[1]-halide, R[1]-amine or other desired R[1]-reagent under suitable conditions. For example, modified Suzuki conditions involving the use of a Pd(0) mediated-coupling with an aryl boronate in the presence of mild base, such as sodium or potassium carbonate or bicarbonate, in toluene may also afford compounds 40. Compounds 40 can also be prepared using corresponding stannanes or zincates, as is known in the art. Alternatively, desired R[1] groups may be installed onto the D'-ring using conventional methods (not shown), as appreciated by those skilled in the art.

The Examples described hereinafter represent exemplary methods of synthesizing or preparing desired compounds of Formulas I-IV, intermediates and various starting materials and/or building blocks thereof. It should be appreciated that these methods are merely representative examples and other conventional, known or developed alternative methods may also be utilized. It should also be appreciated that the exemplary compounds are merely for illustrative purposes only and are not to be construed as limiting the scope of the present invention in any manner.

Analytical Methods:

Unless otherwise indicated, all HPLC analyses were run on a Agilent Model 1100 system with an Agilent Technologies Zorbax SB-$C_8$(5μ) reverse phase column (4.6×150 mm; Part no. 883975-906) run at 30° C. with a flow rate of about 1.50 mL/min. The mobile phase used solvent A ($H_2O$/0.1% TFA) and solvent B (AcCN/0.1% TFA) with a 11 min gradient from 5% to 100% AcCN. The gradient was followed by a 2 min return to 5% AcCN and about a 2.5 minute re-equilibration (flush).

LC-MS Method:

Samples were run on a Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (AcCN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation with a 30×50 mm column at 40 mL/min. The mobile phase used a mixture of solvent A ($H_2O$/0.1% TFA) and solvent B (AcCN/0.1% TFA) with a 15 min gradient from 10% to 95% solvent B. The gradient is followed by a 2 min return to 10% AcCN.

Proton NMR Spectra:

Unless otherwise indicated, all $^1$H NMR spectra were run on a Varian series Mercury 300 MHz or on a Bruker 400 MHz instrument. Where so characterized, all observed protons are reported as parts-per-million (ppm) downfield from tetramethylsilane (TMS) or other internal reference in the appropriate solvent indicated.

Example 1

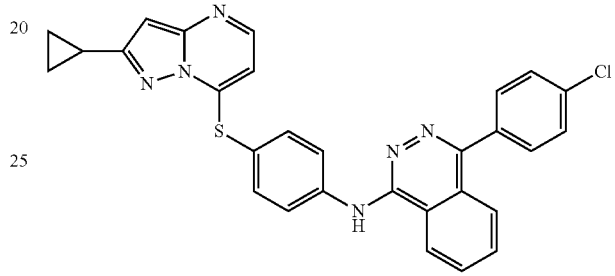

Synthesis of 4-(4-Chlorophenyl)-N-(4-(2-cyclopropylpyrazolo[1,5-a]pyrimidin-7-ylthio)phenyl)phthalazin-1-amine (According to Method A)

Step 1: Sodium 3-ethoxy-3-oxoprop-1-en-1-olate

To a mixture of sodium hydride, 60% (1.07 g, 26.7 mmol) and iPr$_2$O (40 mL) at RT was added ethyl acetate (2.36 ml, 24.1 mmol) in one portion. The internal temperature was adjusted to 40° C. After 5 minutes, ethyl formate (3.87 ml, 48.1 mmol) was added dropwise such that the internal temperature did not rise above 42° C. After the addition was complete, the solution was stirred at RT for 16 hr. The mixture was filtered under Argon and the solid rinsed with hexanes. The resulting white solid, sodium (Z)-3-ethoxy-3-oxoprop-1-en-1-olate, was advanced without further purification.

Step 2: 2-Cyclopropylpyrazolo[1,5-a]pyrimidin-7-ol

A mixture of 5-cyclopropyl-1H-pyrazol-3-amine (415 mg, 3.37 mmol) and sodium (Z)-3-ethoxy-3-oxoprop-1-en-1-olate (0.791 g, 5.73 mmol) in EtOH (3 mL) and toluene (1 mL) was heated to 80° C. in a resealable tube. After 16 hrs the solvent was removed in vacuo. The resulting residue was dissolved in a minimal amount of warm water and triturated with 1 N HCl with cooling (0° C.) until the pH ~1. The resulting solid was filtered and washed with water to afford 2-cyclopropylpyrazolo[1,5-a]pyrimidin-7-ol as an off-white solid that was advanced without further purification. M+H+ found=176.2.

Step 3: 7-Chloro-2-cyclopropylpyrazolo[1,5-a]pyrimidine

A mixture of 2-cyclopropylpyrazolo[1,5-a]pyrimidin-7-ol (0.400 g, 2.28 mmol) and phosphorous oxychloride (4.26 ml, 45.7 mmol) in a resealable tube was heated to 100° C. After 4 hrs the solution was cooled to RT and slowly poured onto ice. The mixture was made basic using 2 N NaOH and saturated NaHCO$_3$ and extracted with EtOAc. The combined organic fractions were washed with brine and dried with sodium sulfate. The organic phase solution was passed over a plug of silica gel and concentrated in vacuo to afford 7-chloro-2-cyclopropylpyrazolo[1,5-a]pyrimidine as a brown oil that was advanced without further purification. MS: Found M+H$^+$ =194.1.

Step 4: 4-(2-Cyclopropylpyrazolo[1,5-a]pyrimidin-7-ylthio)benzenamine

To a mixture of cesium carbonate (0.606 g, 1.86 mmol) and 4-aminobenzenethiol (116 mg, 0.930 mmol) in DMF (3 mL) at RT was added 7-chloro-2-cyclopropylpyrazolo[1,5-a]pyrimidine (0.180 g, 0.930 mmol). The mixture was heated to 60° C. After 2 hrs the mixture was cooled to RT, diluted with EtOAc, and washed with water and brine. After drying the organic fraction with sodium sulfate, the solvent was removed in vacuo to afford 4-(2-cyclopropylpyrazolo[1,5-a] pyrimidin-7-ylthio)benzenamine, which was advanced without further purification. MS: Found M+H$^+$=283.1.

Step 5: 4-(4-Chlorophenyl)-N-(4-(2-cyclopropylpyrazolo[1,5-a]pyrimidin-7-ylthio)phenyl)phthalazin-1-amine A resealable tube charged with a mixture of 4-(2-cyclopropylpyrazolo[1,5-a]pyrimidin-7-ylthio)benzenamine (100 mg, 0.354 mmol) and 1-chloro-4-(4-chlorophenyl)phthalazine (97 mg, 0.354 mmol) in tBuOH (2 mL) was heated to 100° C. After 3 hrs, the mixture was cooled to RT, diluted with CH$_2$Cl$_2$, and washed with water and brine. After drying the organic fraction with sodium sulfate, the solvent was removed in vacuo. The residue was purified by silica gel chromatography using 20-90% Hexanes:EtOAc to afford 4-(4-chlorophenyl)-N-(4-(2-cyclopropylpyrazolo[1,5-a]pyrimidin-7-ylthio)phenyl)phthalazin-1-amine. MS: Found M+H$^+$=521.2.

Example 2

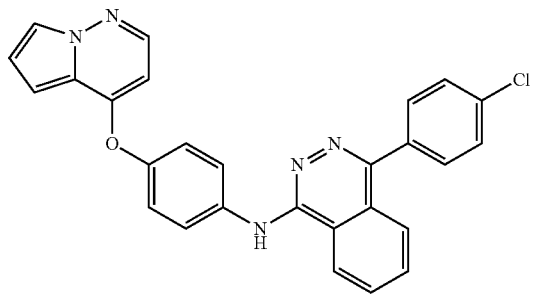 [SMILES: Clc1ccc(-c2nnc(Nc3ccc(Oc4ccnn5cccc45)cc3)c3ccccc23)cc1]

Synthesis of 4-(4-Chlorophenyl)-N-(4-(pyrrolo[1,2-b]pyridazin-4-yloxy)phenyl)-1-phthalazinamine (According to Method B)

Step 1: Ethyl 4-oxo-1,4-dihydropyrrolo[1,2-b]pyridazine-3-carboxylate

Diethyl 2-(ethoxymethylene) malonate (1.82 g, 8.4 mmol) and 1H-pyrrol-1-amine (575 mg, 7.0 mmol) were heated at 125° C. for 2 hours. Diphenyl ether was added and the mixture was heated at 220° C. for two hours, allowing ethanol to distill off. The mixture was then purified by silica gel chromatography using 100% CH$_2$Cl$_2$ to afford ethyl 4-oxo-1,4-dihydropyrrolo[1,2-b]pyridazine-3-carboxylate. MS: Found M+H$^+$=161.

Step 2: Pyrrolo[1,2-b]pyridazin-4(1H)-one

Ethyl 4-oxo-1,4-dihydropyrrolo[1,2-b]pyridazine-3-carboxylate (412 mg, 2.00 mmol), sodium chloride (200 mg), water (1 mL), and DMSO (1 mL) were heated at 150° C. for 3 hours. The solvent was concentrated in vacuo and the residue was purified using 0-50% EtOAc/Hexanes to provide pyrrolo[1,2-b]pyridazin-4(1H)-one. MS: Found M+H$^+$=135.

Step 3: 4-(4-Nitrophenoxy)H-pyrrolo[1,2-b]pyridazine

Pyrrolo[1,2-b]pyridazin-4(1H)-one (110 mg, 820 μmol), 1-fluoro-4-nitrobenzene (174 mg, 1.23 mmol), and 1,4-diazabicyclo[2.2.2]octane (184 mg, 1.64 mmol) were combined in acetonitrile (3 ml) and heated for 72 hours at 80° C. The mixture was concentrated and purified using 100% CH$_2$Cl$_2$ to afford 4-(4-nitrophenoxy)H-pyrrolo[1,2-b]pyridazine.

Step 4: 4-(H-pyrrolo[1,2-b]pyridazin-4-yloxy)benzenamine

To a solution of 4-(4-nitrophenoxy)H-pyrrolo[1,2-b]pyridazine (100 mg, 392 μmol) in MeOH (5 mL) at RT was added 10% palladium on carbon (42 mg). After 18 hrs, the mixture was filtered and concentrated to afford crude 4-(H-pyrrolo[1,2-b]pyridazin-4-yloxy)benzenamine that was advanced without further purification. MS: Found M+H$^+$=226.

Step 5: 4-(4-chlorophenyl)-N-(4-(pyrrolo[1,2-b]pyridazin-4-yloxy)phenyl)-1-phthalazinamine The title compound was prepared from 4-(H-pyrrolo[1,2-b]pyridazin-4-yloxy)benzenamine by a method analogous to that described in Example 1, step 5.

Example 3

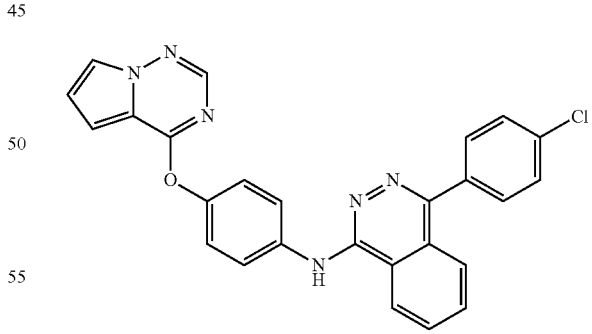

Synthesis of 4-(4-Chlorophenyl)-N-(4-(pyrrolo[2,1-f][1,2,4]triazin-4-yloxy)phenyl)-1-phthalazinamine (According to Method C)

Step 1: 1-Amino-1H-pyrrole-2-carbonitrile

1H-Pyrrole-2-carbaldehyde (12.5 g, 131 mmol) and hydroxylamine-O-sulfonic acid (52.0 g, 460 mmol) were combined in water (400 mL) and stirred at RT for 1 hr. The solution was cooled to 0° C. and a solution of potassium hydroxide (147.0 g, 2.62 mol) in water (500 mL) was added over 1 hr. After 18 hrs at 0° C., the mixture was filtered. The solids were washed with water, and the filtrate was extracted with $CH_2Cl_2$. The organic layer was dried with sodium sulfate, combined with the collected solid, and concentrated in vacuo. The solid was purified by silica gel chromatography using 0-40% EtOAc/Hexanes to afford 1-amino-1H-pyrrole-2-carbonitrile. MS: Found $M+H^+$=108.

Step 2: 1-Amino-1H-pyrrole-2-carboxamide

A solution of 1-amino-1H-pyrrole-2-carbonitrile (100 mg, 0.934 mmol) and potassium hydroxide (1.26 g, 22.5 mmol) in water (3 mL) was stirred at RT for 6 hours. The resulting mixture was then cooled to 0° C. and filtered. The collected solid was washed with cold water until the washings were pH neutral and purified by silica gel chromatography using 0-100% of 90/10/1 $CH_2Cl_2$/MeOH/$NH_4OH$ in $CH_2Cl_2$ to afford 1-amino-1H-pyrrole-2-carboxamide.

Step 3: 1-Formamido-1H-pyrrole-2-carboxamide

To a mixture of 1-Amino-1H-pyrrole-2-carboxamide (1.00 g, 8.0 mmol) and sodium acetate (1.60 g, 20.0 mmol) was added formic acid (11.0 ml, 287 mmol). The mixture was stirred overnight at RT. After removing the excess formic acid in vacuo, water (5 mL) was added and the mixture was cooled to 0° C. The mixture was filtered and the solid washed with water and dried in vacuo to afford 1-formamido-1H-pyrrole-2-carboxamide which was advanced without further purification.

Step 4: Pyrrolo[1,2-f][1,2,4]triazin-4(3H)-one

To a solution of sodium methoxide (5.8 mg, 0.11 mmol) in MeOH (3 mL) was added 1-formamido-1H-pyrrole-2-carboxamide (50.0 mg, 0.327 mmol) and the mixture was refluxed overnight. After cooling to RT, the base was neutralized with one equivalent of HCl in dioxane (4 M). The solvent was removed in vacuo and the residue purified by silica gel chromatography using 0-40% MeOH in $CH_2Cl_2$ to afford pyrrolo[1,2-f][1,2,4]triazin-4(3H)-one.

Step 5: 4-Bromopyrrolo[1,2-f][1,2,4]triazines

Pyrrolo[1,2-f][1,2,4]triazin-4(3H)-one (50 mg, 0.37 mmol) and phosphorus oxybromide (250 mg, 0.87 mmol) were combined and heated at 60° C. for 30 minutes. The resulting semi-solid was cooled and slowly mixed with ice-water with vigorous stirring. The mixture was neutralized with saturated sodium carbonate and extracted with ethyl acetate. The combined organic fractions were dried with sodium sulfate and concentrated in vacuo to afford crude 4-bromopyrrolo[1,2-f][1,2,4]triazines that was advanced without further purification.

Step 6: 4-(4-Chlorophenyl)-N-(4-(pyrrolo[2,1-f][1,2,4]triazin-4-yloxy)phenyl)-1-phthalazinamine The title compound was prepared from 4-bromopyrrolo[1,2-f][1,2,4]triazine by a method analogous to that described in Example 1, steps 4 and 5.

Example 4

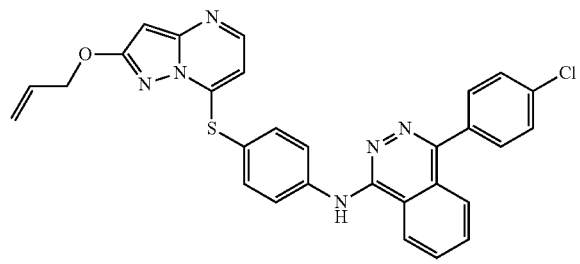 [SMILES: C=CCOc1cc2nccc(Sc3ccc(Nc4nnc(-c5ccc(Cl)cc5)c5ccccc45)cc3)n2n1]

Synthesis of N-(4-(2-(allyloxy)pyrazolo[1,5-a]pyrimidin-7-ylthio)phenyl)-4-(4-chlorophenyl)phthalazin-1-amine (According to Method D)

Step 1: 2-(5-Hydroxy-1H-pyrazol-3-yl)isoindoline-1,3-dione

To a solution of 3-amino-1H-pyrazol-5-ol (10.00 g, 101 mmol) in THF (300 mL) at RT was added phthalic acid anhydride (14.9 g, 101 mmol) followed by acetic acid (69.3 ml, 1.21 mol). The mixture was heated to reflux. After 4 days, the mixture was concentrated in vacuo to afford a slurry that was cooled to 0° C. and filtered. The solid was rinsed with $Et_2O$ and dried in vacuo to afford 2-(5-hydroxy-1H-pyrazol-3-yl)isoindoline-1,3-dione as a yellow solid that was advanced without further purification. MS: Found $M+H^+$=230.2.

Step 2A: 5-(Allyloxy)-1H-pyrazol-3-amine

To a mixture of triphenylphosphine (2.75 g, 10.5 mmol), allyl alcohol (0.714 ml, 10.5 mmol), and 2-(5-hydroxy-1H-pyrazol-3-yl)isoindoline-1,3-dione (2.000 g, 8.73 mmol) in DMF (25 mL) at RT was slowly added DIAD (2.04 ml, 10.5 mmol). After 18 hrs the solution was concentrated in vacuo, diluted with EtOAc, and washed with water and brine. The organic fraction was dried with sodium sulfate, concentrated in vacuo, and purified by silica gel chromatography using 40-70% Hexanes:EtOAc to afford 2-(5-(allyloxy)-1H-pyrazol-3-yl)isoindoline-1,3-dione as a light yellow solid. MH+=270.1. Step 2B: To a mixture of 2-(5-(allyloxy)-1H-pyrazol-3-yl)isoindoline-1,3-dione (0.684 g, 2.54 mmol) in EtOH (10 mL) at RT was added anhydrous hydrazine (0.319 ml, 10.2 mmol). The solution was heated at 50° C. for 18 hrs before cooling to 0° C. The resulting precipitate was removed by filtration. The filtrate was concentrated in vacuo to afford crude 5-(allyloxy)-1H-pyrazol-3-amine that was advanced without further purification. MS: Found M+H$^+$=147.2.

Steps 3-7: N-(4-(2-(allyloxy)pyrazolo[1,5-a]pyrimidin-7-ylthio)phenyl)-4-(4-chlorophenyl)phthalazin-1-amine The title compound was prepared in a manner analogous to that described in Example 1, Steps 2-6.

Example 5

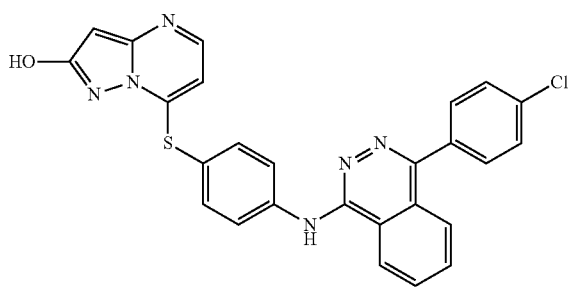 [SMILES: Oc1cc2nccc(Sc3ccc(Nc4nnc(-c5ccc(Cl)cc5)c5ccccc45)cc3)n2n1]

Synthesis of 7-(4-(4-(4-Chlorophenyl)phthalazin-1-ylamino)phenylthio)pyrazolo[1,5-a]pyrimidin-2-ol (According to Method D)

To a mixture of N-(4-(2-(allyloxy)pyrazolo[1,5-a]pyrimidin-7-ylthio)phenyl)-4-(4-chlorophenyl)phthalazin-1-amine (0.110 g, 0.20 mmol, Example 4) and ammonium formate (130 mg, 2.0 mmol) in MeOH (7 mL) was added a slurry of 10% palladium on carbon, (44 mg) in EtOAc (1 mL). The mixture was heated to 65° C. After 8 hrs, the mixture was cooled to RT, filtered over celite, concentrated in vacuo, and purified by silica gel chromatography using 5-15% MeOH in CH$_2$Cl$_2$ with 1% NH$_4$OH to afford 7-(4-(4-(4-chlorophenyl)phthalazin-1-ylamino)phenylthio)pyrazolo[1,5-a]pyrimidin-2-ol as a light yellow solid. MS: Found M+H$^+$=497.0.

Example 6

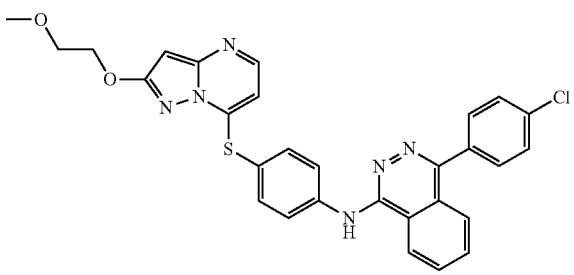 [SMILES: COCCOc1cc2nccc(Sc3ccc(Nc4nnc(-c5ccc(Cl)cc5)c5ccccc45)cc3)n2n1]

Synthesis of 4-(4-Chlorophenyl)-N-(4-(2-(2-methoxyethoxy)pyrazolo[1,5-a]pyrimidin-7-ylthio)phenyl)phthalazin-1-amine (According to Method E)

Step 1: 5-(2-methoxyethoxy)-1H-pyrazol-3-amine

To a mixture of 2-methoxyethanol (0.664 mL, 8.41 mmol) and 3-amino-5-hydroxypyrazole (1.00 g, 10.1 mmol) in C$_6$H$_6$ (50 mL) at RT was added cyanomethylenetri-n-butylphosphorane (2.03 g, 8.41 mmol). The mixture was heated to 90° C. in a pressure vessel. After 16 hrs, the solvent was removed in vacuo. The residue was taken up in CH$_2$Cl$_2$ and adsorbed onto silica gel prior to purification by silica gel chromatography using 2-10% MeOH in CH$_2$Cl$_2$ with 1% NH$_4$OH to afford 5-(2-methoxyethoxy)-1H-pyrazol-3-amine as a yellow oil. MH+=158.2.

Steps 2-7: 4-(4-chlorophenyl)-N-(4-((2-((2-(methyloxy)ethyl)oxy)pyrazolo[1,5-a]pyrimidin-7-yl)thio)phenyl)-1-phthalazinamine The title compound, 4-(4-chlorophenyl)-N-(4-(2-(2-methoxyethoxy)pyrazolo[1,5-a]pyrimidin-7-ylthio)phenyl)phthalazin-1-amine, was prepared by a method analogous to that described in Example 1.

Example 7

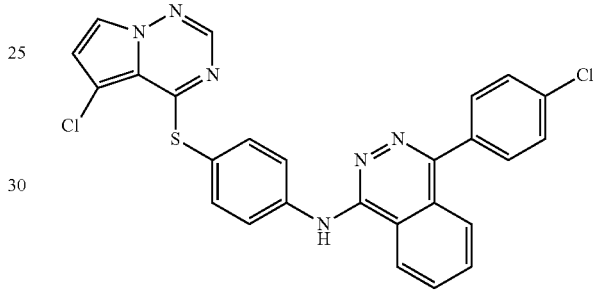

Synthesis of 4-(4-Chlorophenyl)-N-(4-(5-chloropyrrolo[1,2-f][1,2,4]triazin-4-ylthio)phenyl)phthalazin-1-amine (According to Method F)

Step 1: Methyl 1-amino-3-chloro-1H-pyrrole-2-carboxylate hydrochloride

To a mixture of methyl 3-chloro-1H-pyrrole-2-carboxylate (2.50 g, 15.7 mmol) and DMF (10 mL) at 0° C. was added 60% sodium hydride (0.816 g, 20.4 mmol). After 15 min, O-(2,4-dinitrophenyl)hydroxylamine (3.74 g, 18.8 mmol) was added and the mixture was stirred at 0° C. for 1 hr before warming to RT. After 18 hrs, the mixture was diluted with 10% NaCl and extracted with EtOAc. The organic fractions were dried with sodium sulfate and purified by silica gel chromatography using 10-30% Hexanes:EtOAc to afford a crude, brown oil. The oil was taken up in Et$_2$O and treated with 4 N HCl in dioxane. The resulting off-white precipitate was collected by filtration to afford methyl 1-amino-3-chloro-1H-pyrrole-2-carboxylate hydrochloride.

Step 2: 5-Chloropyrrolo[1,2-f][1,2,4]triazin-4(3H)-one

A solution of methyl 1-amino-3-chloro-1H-pyrrole-2-carboxylate hydrochloride (2.00 g, 9.48 mmol) and formamide (11.3 ml, 284 mmol) was exposed to microwave radiation at 170° C. for 45 min. Upon cooling to RT the solution solidified. The slurry was diluted with EtOAc and heated until all solids dissolved. Upon cooling and concentration in vacuo, 5-chloropyrrolo[1,2-f][1,2,4]triazin-4(3H)-one crystallized from the solution as an off-white solid. MS: Found M+H+= 170.1.

Steps 3-7: 4-(4-Chlorophenyl)-N-(4-(5-chloropyrrolo [1,2-f][1,2,4]triazin-4-ylthio)phenyl)phthalazin-1-amine The title compound was prepared by a method analogous to that described in Example 1. MS data is provided in Table 1.

Example 8

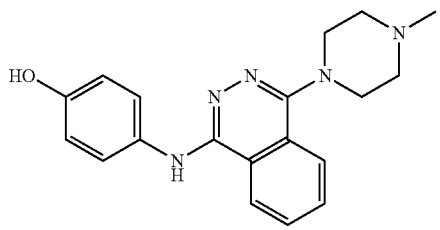 [SMILES: CN1CCN(c2nnc(Nc3ccc(O)cc3)c3ccccc23)CC1]

Synthesis of 4-(4-(4-methylpiperazin-1-yl)phthalazin-1-ylamino)phenol

A mixture of 4-aminophenol (42 mg, 0.38 mmol), 1-chloro-4-(4-methylpiperazin-1-yl)phthalazine (100 mg, 0.381 mmol), and TFA (29 µl, 0.38 mmol) was heated in 2-butanol (3 mL) in a sealed tube at 90° C. overnight. Next day LC/MS shows completion of reaction. The reaction was cooled and diluted with DCM. Aqueous sodium bicarbonate was added and the organic layer was collected. The aqueous layer was neutralized with 1N HCl and the product was extracted with DCM. The organic layers were combined, dried over sodium sulfate, and concentrated to afford 4-(4-(4-methylpiperazin-1-yl)phthalazin-1-ylamino)phenol as solid brown material. MS: Found M+H+=336.2. Calc'd for $C_{19}H_{21}N_5O$: 335.4.

Example 9

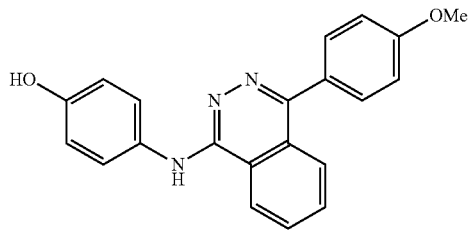 [SMILES: COc1ccc(-c2nnc(Nc3ccc(O)cc3)c3ccccc23)cc1]

Synthesis of 4-(4-(4-methoxyphenyl)phthalazin-1-ylamino)phenol hydrochloride

4-Aminophenol (340 mg, 3.1 mmol), 1-chloro-4-(4-methoxyphenyl)phthalazine (837 mg, 3.1 mmol), and sec-butanol (12 mL, 3.1 mmol) were combined in a resealable tube and heated to 100° C. overnight. The reaction progress was monitored by LCMS, and upon completion, the orange reaction was cooled diluted with diethyl ether. The resulting precipitate was filtered and washed with diethyl ether, and the solid was dried in vacuo to provide 4-(4-(4-methoxyphenyl)phthalazin-1-ylamino)phenol hydrochloride (1.17 g, 100% yield) as an orange solid. MS: Found M+H+=344.0. Calc'd for $C_{19}H_{21}N_5O$: 343.13.

Example 10

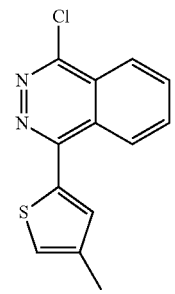 [SMILES: Cc1csc(-c2nnc(Cl)c3ccccc23)c1]

Synthesis of 1-Chloro-4-(4-methylthiophen-2-yl)phthalazine 1,4-Dichlorophthalazine (1.40 g, 7.03 mmol), 4-methylthiophen-2-ylboronic acid (999 mg, 7.03 mmol), and $PdCl_2$ (DPPF) (721 mg, 985 µmol) were added into a sealed tube. The tube was purged with Argon. Then sodium carbonate (2.0 M in water) (7.74 ml, 15.5 mmol) and 1,4-dioxane (35.2 ml, 7.03 mmol) were added. The tube was sealed, stirred at RT for 5 min, and placed in a preheated oil bath at 110° C. After 1 h, LC-MS showed product and byproduct (double coupling), and SM dichlorophthalazine. The reaction was cooled to RT, filtered through a pad of celite with an aid of EtOAc, concentrated, and loaded onto column. The product was purified by column chromatography using Hex to remove the top spot, then 80:20 Hex:EtOAc to collect the product. The product, 1-chloro-4-(4-methylthiophen-2-yl)phthalazine was obtained as yellow solid. LC-MS showed that the product was contaminated with a small amount of SM dichlorophthalazine and biscoupling byproduct. MS m/z=261 [M+1]+. Calcd for $C_{13}H_9ClN_2S$: 260.12.

Example 11

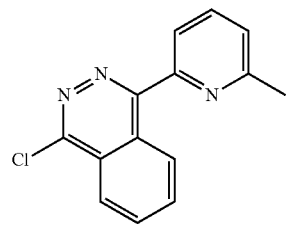 [SMILES: Cc1cccc(-c2nnc(Cl)c3ccccc23)n1]

Synthesis of 1-Chloro-4-(6-methylpyridin-2-yl)phthalazine

Step 1: 2-(Dimethylamino)isoindoline-1,3-dione

The title compound was prepared according to methods described in the following papers: (a) Deniau, E.; Enders. D.;

Couture, A.; Grandclaudon, P. *Tetrahedron: Asymmetry* 2003, 14, 2253. (b) Saito, Y.; Sakamoto, T.; Kikugawa, Y. *Synthesis* 2001, 221. (c) Deniau, E.; Enders, D. *Tetrahedron Lett.* 2000, 41, 2347.

To a solution of isobenzofuran-1,3-dione (5.00 g, 34 mmol) and N,N-dimethylhydrazine (2.9 ml, 37 mmol) in toluene (75 ml, 34 mmol) in a RBF was added p-TsOH.H$_2$O (0.32 g, 1.7 mmol). A Dean-Stark apparatus and a condenser were attached to the RBF. The mixture was refluxed. After 4 h, LCMS showed mainly product. The reaction was cooled to RT. Toluene was removed under reduced pressure, and the crude was dissolved in CH$_2$Cl$_2$, washed with sat NaHCO$_3$, water, and brine. The organic was dried over MgSO$_4$, filtered, and concentrated. Light yellow solid was obtained. $^1$H NMR showed mainly product, 2-(dimethylamino)isoindoline-1,3-dione. MS Calcd for C$_{10}$H$_{10}$N$_2$O$_2$: [M]$^+$=190. Found: [M+H]$^+$=191.

Step 2: 2-(Dimethylamino)-3-hydroxy-3-(6-methylpyridin-2-yl)isoindolin-1-one In a dry RBF, 2-bromo-6-methylpyridine (66 μl, 581 μmol) and THF (1211 μl, 581 μmol) were added. The reaction was purged with argon, and cooled to −78° C. BuLi (244 μl, 610 μmol) was added via syringe. After 30 min, the anion was cannulated into a solution of 2-(dimethylamino)isoindoline-1,3-dione (166 mg, 872 μmol) in 2 mL of THF previously submerged in a cold bath at −78° C. for 2 min (the starting material precipitated out of the solution at low temp). After 15 min at −78° C., the temperature was warmed to −30° C. After 1 h, LCMS showed mainly product at 1.535 min. The reaction was quenched slowly with sat. NH$_4$Cl. The product was extracted with CH$_2$Cl$_2$. The organic layer was washed with brine, dried over MgSO$_4$, filtered, and concentrated to give a yellow oil. The product was purified using 85:15 CH$_2$Cl$_2$:(90:10:1 CH$_2$Cl$_2$:MeOH:NH$_4$OH). Viscous yellow oil was obtained. $^1$H NMR showed mainly product, 2-(dimethylamino)-3-hydroxy-3-(6-methylpyridin-2-yl)isoindolin-1-one. MS Calcd for C$_{16}$H$_{17}$N$_3$O$_2$: [M]$^+$=283. Found: [M+H]$^+$= 284.

Step 3: 4-(6-Methylpyridin-2-yl)phthalazin-1(2H)-one

The title compound was prepared according to a method described in Saito, Y.; Sakamoto, T.; Kikugawa, Y. *Synthesis* 2001, 2, 221. 2-(Dimethylamino)-3-hydroxy-3-(6-methylpyridin-2-yl)isoindolin-1-one (3.18 g, 11.0 mmol), EtOH (11.0 ml, 11.0 mmol), and hydrazine (5.30 ml, 168 mmol) were added into a RBF fitted with a reflux condenser. A nitrogen balloon was attached on top of the condenser. The reaction was refluxed overnight. LCMS showed that the reaction was completed. The reaction was cooled to rt. Off-white solid precipitated out of the solution. Water was added and the mixture was cooled to 0° C. The solid was filtered off with an aid of water and dried under vacuum. White solid was obtained. LCMS of the solid showed product, 4-(6-methylpyridin-2-yl)phthalazin-1(2H)-one. MS Calcd for C$_{14}$H$_{11}$N$_3$O: [M]$^+$=237. Found: [M+H]$^+$=238.

Step 4: 1-Chloro-4-(6-methylpyridin-2-yl)phthalazine

A dry RBF set up with stirring bar and reflux condenser was charged with 4-(6-methylpyridin-2-yl)phthalazin-1 (2H)-one (780 mg, 3.29 mmol) and POCl$_3$ (10.7 ml, 115 mmol). This was stirred under reflux for 18 h. Excess POCl$_3$ was removed under vacuum with an aid of toluene. The residue was cooled to 0° C. and basified with cold 6 N NaOH until pH=9. Occasionally, ice was added to keep the mixture cold to prevent the hydrolysis. Stirring, agitation, and sonication eventually provided a solid material at basic pH. The solids were filtered, washed with ample amount of water and dried under vacuum to afford a white solid. MS Calcd for C$_{14}$H$_{10}$ClN$_3$: [M]$^+$=255. Found: [M+H]$^+$=256.

Example 12

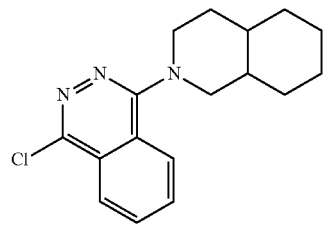 [SMILES: Clc1nnc(N2CCC3CCCCC3C2)c2ccccc12]

Synthesis of 1-chloro-4-(octahydroisoquinolin-2 (1H)-yl)phthalazine

A resealable pressure bottle was charged with 1,4-dichlorophthalazine (1258 mg, 6.28 mmol), decahydroisoquinoline (588 μl, 3.95 mmol), potassium carbonate (546 mg, 3.95 mmol) and DMSO (20 mL, 0.2 M). Reaction was stirred at 80° C. for 16 h, then cooled to RT and diluted with 5 mL of DMSO. The solution was purified by Gilson HPLC (10% to 90% CH$_3$CN/H$_2$O/0.1% TFA) to afford 1-chloro-4-(octahydroisoquinolin-2(1H)-yl)phthalazine. MS [M+H]=302.1. Calcd for C$_{17}$H$_{20}$ClN$_3$: 301.8.

Example 13

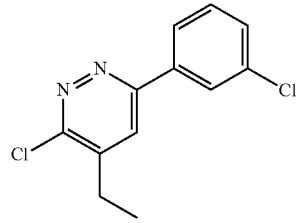 [SMILES: CCc1cc(-c2cccc(Cl)c2)nnc1Cl]

Synthesis of 3-chloro-6-(3-chlorophenyl)-4-ethylpyridazine

Step 1: 4-(3-chlorophenyl)-2-ethyl-2-hydroxy-4-oxobutanoic acid

A RBF was charged with 2-oxobutanoic acid (2.50 g, 24.5 mmol) and 3.2 mL of water and the mixture was cooled to 0° C. The acid was neutralized by slow addition of 20% aqueous KOH. 3'-chloroacetophenone (3.79 g, 24.5 mmol) was added, followed by a 1.3 M solution of KOH (2.20 g, 39.2 mmol) in MeOH. The reaction mixture was stirred at 0° C. for 48 h. The mixture was brought to pH 2 by dropwise addition of conc. H$_2$SO$_4$. The MeOH was removed in vacuo, and 25 mL of water was added. The heterogeneous mixture was filtered through Celite, and the filter cake was washed with water and CH$_2$Cl$_2$. The layers of the filtrate were separated, and the aqueous portion was extracted with additional CH$_2$Cl$_2$. The combined organics were dried with MgSO$_4$, filtered and concentrated to a volume of ~25 mL. Hexane was added until the mixture became cloudy, and upon standing a white crystalline solid formed. The mother liquor was decanted and the solids were washed with hexane and dried to provide 4-(3-chlorophenyl)-2-ethyl-2-hydroxy-4-oxobutanoic acid as a white crystalline solid. MS m/z=279 [M+Na]$^+$. Calc'd for C$_{12}$H$_{13}$ClO$_4$: 256.69.

Step 2:
6-(3-chlorophenyl)-4-ethylpyridazin-3(2H)-one

A RBF was charged with 4-(3-chlorophenyl)-2-ethyl-2-hydroxy-4-oxobutanoic acid (2.78 g, 10.8 mmol), hydrazine (0.510 ml, 16.2 mmol) and 11 mL of n-BuOH. A Dean-Stark apparatus fitted with a reflux condenser was attached, and the mixture was heated under nitrogen at 130° C. for 15 h. Upon cooling a precipitate formed, which was filtered, washed with cold EtOH, and dried. 6-(3-chlorophenyl)-4-ethylpyridazin-3(2H)-one was isolated as a white solid. MS m/z=235 [M+H]$^+$. Calc'd for C$_{12}$H$_{11}$ClN$_2$O: 234.68.

Step 3:
3-chloro-6-(3-chlorophenyl)-4-ethylpyridazine

A RBF was charged with 6-(3-chlorophenyl)-4-ethylpyridazin-3(2H)-one (1.50 g, 6.4 mmol) and phosphorus oxychloride (6.0 ml, 64 mmol). Hunig's base (1.2 ml, 7.0 mmol) was added to the mixture dropwise (slightly exothermic). The flask was fitted with a reflux condenser and a nitrogen inlet and the mixture was heated at 110° C. for 3 h. Upon cooling the reaction mixture was poured onto ice. 6N NaOH was added dropwise until pH 9 while keeping the mixture cold by gradual addition of ice. The solids were filtered, washed with water and dried to provide 3-chloro-6-(3-chlorophenyl)-4-ethylpyridazine as a peach colored solid. MS m/z=253 [M]$^+$. Calc'd for C$_{12}$H$_{10}$Cl$_2$N$_2$: 253.13.

Example 14

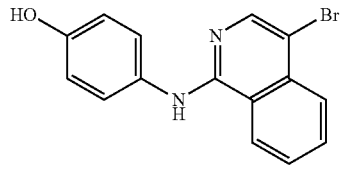 [SMILES: Oc1ccc(Nc2ncc(Br)c3ccccc23)cc1]

Synthesis of
4-(4-bromoisoquinolin-1-ylamino)phenol hydrochloride

A mixture of 4-aminophenol (225 mg, 2062 µmol) and 4-bromo-1-chloroisoquinoline (500 mg, 2062 µmol) was heated in sec-butanol (15 mL) in a sealed tube at 100° C. for 2 hours. TFA (477 µl, 6186 µmol) was added and the reaction mixture was allowed to stir at 100° C. overnight. LCMS analysis showed conversion to 4-(4-bromoisoquinolin-1-ylamino)phenol hydrochloride. The dark red reaction mixture was cooled, and diethyl ether was added. The resulting precipitate was filtered and washed with diethyl ether, and the solid was dried in vacuo to provide 4-(4-bromoisoquinolin-1-ylamino)phenol hydrochloride as a purple solid.

Example 15

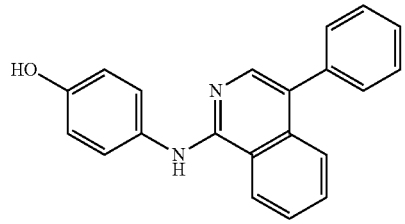 [SMILES: Oc1ccc(Nc2ncc(-c3ccccc3)c3ccccc23)cc1]

Synthesis of
4-(4-phenylisoquinolin-1-ylamino)phenol

To a solution of 4-(4-bromoisoquinolin-1-ylamino)phenol (578 mg, 1834 µmol), phenylboronic acid (335 mg, 2751 µmol), and tetrakis (triphenylphosphine) palladium (0) (212 mg, 183 µmol) in toluene (10480 µl, 1834 µmol) and ethanol (2620 µl, 1834 µmol) was added sodium carbonate (6281 µl, 12563 µmol) in water (2M). The reaction mixture was heated to 100° C. overnight. The reaction progress was monitored by LCMS, which showed conversion to 4-(4-phenylisoquinolin-1-ylamino)phenol. The product was purified by silica gel chromatography (eluent: hexanes:EtOAc 0-50%) to yield 4-(4-phenylisoquinolin-1-ylamino)phenol.

Example 16

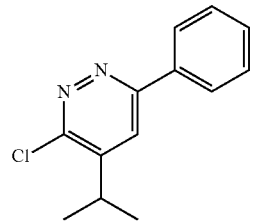 [SMILES: CC(C)c1cc(-c2ccccc2)nnc1Cl]

Synthesis of
3-chloro-4-isopropyl-6-phenylpyridazine

A RBF was charged with 3-chloro-4-ethyl-6-phenylpyridazine (250 mg, 1.143 mmol) and 5.7 mL of THF, and the mixture was cooled to −78° C. under nitrogen. Lithium diisopropylamide, 2.0 M solution in heptane/tetrahydrofuran/ethylbenzene (0.686 mL, 1.372 mmol) was added, and the mixture was stirred for 5 min at −78° C., followed by 1 h at room temperature. The mixture was cooled back down to −78° C., and methyl iodide (195 mg, 1.372 mmol) that had been passed through a plug of basic alumina prior to use was added dropwise. The reaction was stirred at this temperature for 5 min, followed by RT for 0.5 h. After quenching with water, the solution was diluted with CH$_2$Cl$_2$ and the layers were separated. The aqueous portion was extracted with additional CH$_2$Cl$_2$ and the combined organics were dried with MgSO$_4$, filtered and concentrated. The crude material was purified by silica gel chromatography (CH$_2$Cl$_2$— 10% MeOH/CH$_2$Cl$_2$) to provide 3-chloro-4-isopropyl-6-phenylpyridazine as a colorless oil, which crystallized upon standing. MS m/z=233 [M+H]$^+$. Calc'd for C$_{13}$H$_{13}$ClN$_2$: 232.71.

Examples 17-19

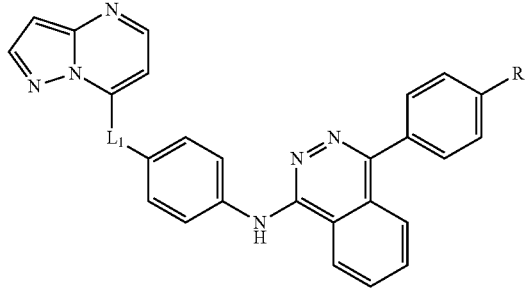

The chloro-pyrazolo-pyrimidine intermediate, for preparation of examples 17-19, was prepared by a procedure analogous to that described in Senga, K.; et al. *J. Med. Chem.* 1981, 24, 610-613.

Example 17 is the compound above wherein L$^1$=O and R is H.

Example 18 is the compound above wherein L$^1$=S and R is H.

Example 19 is the compound above wherein L$^1$=S and R is Cl.

The Examples disclosed in Table I below are additional representative examples, of the present invention. The Examples were made by the methods indicated in Table I, which generally correlate to Methods A, B, C, D, E and F of Schemes 1-6 and Examples 1-7 herein. The MS data is the M+H$^+$ ion value found for the example. Biological data is provided for those compounds exemplified in Table I. Blanks indicate that no data is available.

TABLE 1

| Ex. No. | Name | MS Data | Method | AurA_IC$_{50}$_IP (Avg) | AurB_IC$_{50}$_IP (Avg) | 24 h_4N Ploidy EC$_{50}$_IP (Avg) |
|---|---|---|---|---|---|---|
| 20 | 4-(5-chloro-2-pyridinyl)-N-(4-(pyrazolo[1,5-a]pyrimidin-7-ylthio)phenyl)-1-phthalazinamine | 482.0 | A | ++++ | ++++ | ++++ |
| 21 | 4-(5-methyl-2-pyridinyl)-N-(4-(pyrazolo[1,5-a]pyrimidin-7-ylthio)phenyl)-1-phthalazinamine | 462.1 | A | ++++ | ++++ | ++++ |
| 1 | 4-(4-chlorophenyl)-N-(4-((2-cyclopropylpyrazolo[1,5-a]pyrimidin-7-yl)thio)phenyl)-1-phthalazinamine | 521.2 | A | + | ++++ | ++++ |
| 22 | N-(4-((2-cyclopropylpyrazolo[1,5-a]pyrimidin-7-yl)thio)phenyl)-4-phenyl-1-phthalazinamine | 487.1 | A | +++ | ++++ | ++++ |
| 23 | N-(4-((2-cyclopropylpyrazolo[1,5-a]pyrimidin-7-yl)thio)phenyl)-4-(4-methyl-2-thienyl)-1-phthalazinamine | 507.1 | A | ++++ | +++ | ++++ |
| 2 | 4-(4-chlorophenyl)-N-(4-(pyrrolo[1,2-b]pyridazin-4-yloxy)phenyl)-1-phthalazinamine | 464.0 | B | +++ | ++++ | +++ |
| 3 | 4-(4-chlorophenyl)-N-(4-(pyrrolo[2,1-f][1,2,4]triazin-4-yloxy)phenyl)-1-phthalazinamine | 465.1 | C | ++ | ++++ | ++ |
| 24 | 4-(4-methyl-2-thienyl)-N-(4-(pyrrolo[2,1-f][1,2,4]triazin-4-yloxy)phenyl)-1-phthalazinamine | 451.1 | C | +++ | ++++ | +++ |
| 25 | 4-(4-chlorophenyl)-N-(4-(pyrrolo[2,1-f][1,2,4]triazin-4-ylthio)phenyl)-1-phthalazinamine | 481.1 | C | + | ++++ | +++ |
| 26 | 4-(4-methyl-2-thienyl)-N-(4-(pyrrolo[2,1-f][1,2,4]triazin-4-ylthio)phenyl)-1-phthalazinamine | 467.0 | C | ++ | ++++ | +++ |
| 4 | 4-(4-chlorophenyl)-N-(4-((2-(2-propen-1-yloxy)pyrazolo[1,5-a]pyrimidin-7-yl)sulfanyl)phenyl)-1-phthalazinamine | 537.0 | D | | | +++ |

TABLE 1-continued

| Ex. No. | Name | MS Data | Method | AurA_IC$_{50}$_IP (Avg) | AurB_IC$_{50}$_IP (Avg) | 24 h_4N Ploidy EC$_{50}$_IP (Avg) |
|---|---|---|---|---|---|---|
| 27 | N-(4-((2-((2-(methyloxy)ethyl)oxy)pyrazolo[1,5-a]pyrimidin-7-yl)thio)phenyl)-4-phenyl-1-phthalazinamine | 521.2 | E | +++ | ++++ | ++++ |
| 28 | N-(4-((2-((2-(methyloxy)ethyl)oxy)pyrazolo[1,5-a]pyrimidin-7-yl)thio)phenyl)-4-(4-methyl-2-thienyl)-1-phthalazinamine | 541.2 | E | ++++ | ++++ | ++++ |
| 6 | 4-(4-chlorophenyl)-N-(4-((2-((2-(methyloxy)ethyl)oxy)pyrazolo[1,5-a]pyrimidin-7-yl)thio)phenyl)-1-phthalazinamine | 555.1 | E | ++++ | ++++ | ++++ |
| 5 | 7-((4-((4-(4-chlorophenyl)-1-phthalazinyl)amino)phenyl)thio)pyrazolo[1,5-a]pyrimidin-2-ol | 497.0 | D | ++++ | ++++ | +++ |
| 29 | N-(4-((5-chloropyrrolo[2,1-f][1,2,4]triazin-4-yl)thio)phenyl)-4-phenyl-1-phthalazinamine | 481.2 | F | + | ++++ | +++ |
| 7 | 4-(4-chlorophenyl)-N-(4-((5-chloropyrrolo[2,1-f][1,2,4]triazin-4-yl)thio)phenyl)-1-phthalazinamine | 515.0 | F | + | ++++ | +++ |

The invention further provides methods for making compounds of Formulas I-IV. For example, and in one embodiment, there is provided a method of making a compound of Formula I, the method comprising the step of reacting compound of Formula A

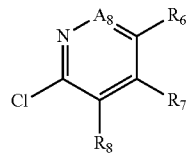

with a compound of Formula B

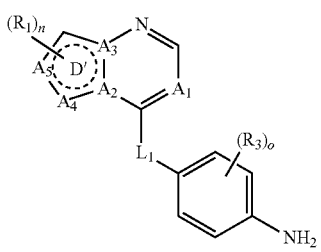

wherein $A^8$ and $R^{6-8}$ of the compound of formula A and $A^1$, $A^2$, $A^3$, $A^4$, $A^5$, $L^1$, $R^1$, $A^3$ and n and o of the compound of formula B are as defined herein, to make a compound of Formula I. This method may also be used to make a compound of Formulas II, III and IV.

While the examples described above provide processes for synthesizing compounds of Formulas I-IV, other methods may be utilized to prepare such compounds. In the procedures described herein, the steps may be performed in an alternate order and may be preceded, or followed, by additional protection/deprotection steps as necessary.

Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, 4$^{th}$ edition, Volume 15/1, Georg Thieme Verlag, Stuttgart (1974), in H.-D. Jakubke and H. Jescheit, Aminosäuren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide and Derivate (Chemistry of Carbohydrates: Monosaccharides and Derivatives), Georg Thieme Verlag, Stuttgart (1974).

The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like, many of which were utilized in the Examples above. Reactions conditions such as temperature, duration, pressure, and atmosphere (inert gas, ambient) are known in the art and may be adjusted as appropriate for the reaction.

All synthetic procedures described herein can be carried out either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further includes salt forms of compounds of Formulas I, II, III and IV. Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Suitable acid and base addition salts are further described in the Definition Section herein.

The invention further encompasses pro-drugs of compounds of Formulas I, II, III and IV. For example, a phosphate group may be a pro-drug derivative of an alcohol group or an amine group, or an ester may be a pro-drug of a carboxylic acid functional group. Phosphate groups may be incorporated into desired compounds of Formulas I, II, III and IV in order to improve upon in-vivo bioavailability and/or other pharmacokinetic or pharmacodynamic properties of the compound.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention structures resulting from processing the compounds of the invention in situ are also within the scope of the invention.

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with chiral reagents, such as an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The synthetic chemistry transformations, as well as protecting group methodologies (protection and deprotection) described above and useful in synthesizing the inhibitor compounds described herein, are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Biological Evaluation

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

Although the pharmacological properties of the compounds of the invention (Formulas I-IV) vary with structural change, in general, activity possessed by compounds of Formulas I-IV may be demonstrated both in vitro as well as in vivo. The following exemplified pharmacological assays have been carried out with the compounds according to the invention. Briefly, representative compounds of the invention were found to inhibit the activity of Aurora kinase selectively or non-selectively. This activity demonstrates the utility of the compounds in the prophylaxis and treatment of cellular proliferative disorders, including cancer, as described herein.

Aurora Kinase HTRF Assays

AuroraA-TPX2-Homogeneous Time Resolved Fluorescent (HTRF) Kinase Assay:

The Aurora-A HTRF assay begins with Aurora-A in the presence of ATP phosphorylating the biotinylated peptide PLK. The reaction incubates for about 120 min. Detection reagents are added to quench the reaction. These agents stop the reaction by diluting out the enzyme and chelating the metals due to the presence of EDTA. After addition, the assay is incubated overnight to allow the detection reagents to equilibrate.

The AuroraA HTRF assay comprises 1 µL of compound in 100% DMSO, 20 µL of ATP and biotinylated PLK, and 20 µL of AuroraA-TPX2 KD GST for a final volume of about 41 µL. The final concentration of PLK is about 1 µM. The final concentration of ATP is about 1 µM (Km(app)=1 µM+/−0.1) and the final concentration of AuroraA is about 5 nM. Buffer conditions are as follows: 60 mM HEPES pH 7.5, 25 mM NaCl, 10 mM MgCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0005 mg/mL, and europilated anti-phosphoPLK Ab (Eu-anti-PLK) at a final conc of 0.02 nM.

The assay plate is read in either a Discovery or a RubyStar. The eu-anti-PLK is excited at 320 nm and emits at 615 nm to excite the SA-APC which in turn emits at 655 nm. The ratio of SA-APC at 655 nm (excited due to close proximity to the Eu-anti-PLK because of phosphorylation of the peptide) to free Eu-anti-PLK at 615 nm will give substrate phosphorylation.

Many of the Examples described herein were tested, and found to be active compounds. Table I includes related biological data, which may be interpreted using the activity gauge below:

"+" represents an activity ($IC_{50}$) of >2.5 uM;
"++" represents an activity ($IC_{50}$) in the range of 2.5 uM-500 nM;
"+++" represents an activity ($IC_{50}$) in the range of 500-100 nM; and
"++++" represents an activity ($IC_{50}$) of less than 100 nM.
Selected Examples 1-7 and 17-29 exhibited good potency in the Aurora kinase A HTRF assay.

AuroraB-Homogeneous Time Resolved Fluorescent (HTRF) Kinase Assay:

The AuroraB HTRF assay begins with AuroraB in the presence of ATP phosphorylating the biotinylated peptide Histone H3. The reaction incubates for about 90 min. the reaction is quenched by addition of detection reagents, which stop the reaction by diluting out the enzyme and chelating the metals due to the presence of EDTA. After addition, the assay is incubated for about 60 min to allow detection reagents to equilibrate.

The AuroraB HTRF assay comprises 1 μL of compound in 100% DMSO, 20 μL of ATP and biotinylated Histone H3, and 20 μL of AuroraB FL His for a final volume of 41 μL. The final concentration of Histone H3 is 0.1 μM. The final concentration of ATP is 23 μM (Km(app)=23 μM+/−2.6) and the final concentration of AuroraB is 400 pM. Buffer conditions are as follows: 50 mM HEPES pH 7.5, 5 mM NaCl, 0.5 mM MgCl, 0.5 mM MnCl, 2 mM DTT, 0.05% BSA.

The assay is quenched and stopped with 160 μL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.001 mg/mL, and europilated anti-phosphoHistoneH3 Ab (Eu-anti-His H3) at a final conc of 0.064 nM.

The assay plate is read in either a Discovery or a RubyStar. The eu-anti-His H3 is excited at 320 nm and emits at 615 nm to excite the SA-APC which in turn emits at 655 nm. The ratio of SA-APC at 655 nm (excited due to close proximity to the Eu-anti-His H3 because of phosphorylation of the peptide) to free Eu-anti-His H3 at 615 nm will give substrate phosphorylation.

Many of the Examples described herein were tested, and found to be active compounds. Table I includes related biological data, which may be interpreted using the activity gauge below:

"+" represents an activity ($IC_{50}$) of >2.5 uM;
"++" represents an activity ($IC_{50}$) in the range of 2.5 uM-500 nM;
"+++" represents an activity ($IC_{50}$) in the range of 500-100 nM; and
"++++" represents an activity ($IC_{50}$) of less than 100 nM.
Selected Examples 1-7 and 17-29 exhibited good potency in the Aurora kinase B HTRF assay.

Aurora Kinase Cell-Based Assay

HeLa Cell 24 hr Ploidy Assay Protocol

The purpose of this assay is to evaluate the ability of selected individual compounds to induce Deoxyribonucleic acid (DNA) content (ploidy) in cells thought failed cell division. Cell cycle analysis is a rapid and efficient way to evaluate the status of DNA content (ploidy) of a given cell. HeLa cells ($1 \times 10^4$ HeLa cells/well) in 100 ul of media (MEM+10% FBS) were plated in 96-well plates (Packard View) and cultured for 24 hrs at 37° C. maintained in a 5% $CO_2$ atmosphere. The following day, cells were treated for 24 hrs with inhibitor compounds (10 pt. Dose ranging from 0.0024-1.25 umol/L). The compounds were serially diluted in DMSO (0.25% final concentration). The cells were fixed (3.7% Formaldehyde and 1% glutaraldehyde) and permeabilized (1×PBS with 1% BSA and 0.2% Triton X-100) in preparation for nuclear staining. The well plates were stained for 45 minutes at RT in the dark using Hoechest 33342 nuclear stain at 0.5 ug·ml (Stock of 10 mg/ml, Invitrogen, CA, Cat # H3570). The nuclear stain was removed by aspiration and the cells were washed with wash buffer. A Cellomics Array Scan Vti plate reader was used to acquire the DNA ploidy data of the cells using Cell Cycle bioapplication. Numbers for each of "valid cell count/well", "% of 4N cells" and "% of >4Ncells" were calculated with the assistance of an Activity Base 5.1ca software and dose curves were generated using an XLFit software. With XLFit, final $EC_{50}$ IP and $EC_{50}$ transit values, as well as the Max and Min, were calculated for each curve. Many of the Examples described herein were tested, and fund to be active compounds. Table I includes related biological data in the 24 h cell-ploidy content assay, which may be interpreted using the activity gauge below:

"+" represents an activity ($IC_{50}$) of >2.5 uM;
"++" represents an activity ($IC_{50}$) in the range of 2.5 uM-500 nM;
"+++" represents an activity ($IC_{50}$) in the range of 500-100 nM; and
"++++" represents an activity ($IC_{50}$) of less than 100 nM.
Selected Examples 1-7 and 17-29 exhibited good potency in this cell-based assay.

Indications

The compounds of the invention have Aurora kinase modulatory activity in general, and inhibitory activity in particular. In one embodiment of the invention, there is provided a method of modulating Aurora kinase enzyme in a subject, the method comprising administering to the subject an effective dosage amount of a compound of Formulas I-IV. As such, the compounds of the invention may be used to treat cellular proliferation disorders, including uncontrolled cell growth and aberrant cell cycle regulation. The compounds are also useful for treating disorders related to hyper-proliferation of cells in normal tissue, including without limitation, non-tumor bearing and metastatic tissue. For example, one use may be to protect normal hair follicles from chemotherapy induced alopecia.

In addition, compounds of the invention are useful for, but not limited to, the prevention or treatment of cancer and other Aurora kinase-mediated diseases or disorders. For example, compounds of the invention would be useful for the treatment of various solid and hematologically derived tumors, such as carcinomas, including, without limitation, cancer of the bladder, breast, colon, kidney, liver, lung (including small cell lung cancer), esophagus, gall-bladder, ovary, pancreas, stomach, cervix, thyroid, prostate, skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compound of the invention may also be used to treat chemotherapy-induced thrombocytopenia, since the compounds may increase platelet count be increasing the rate of megakaryocyte maturation.

The compounds would also be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity. The compounds of the invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the invention are also useful in the treatment of cardiovascular conditions such as atherosclerosis, restenosis, arteriosclerosis, vascular occlusion and carotid obstructive disease.

Based on the ability to modulate kinases impacting angiogenesis, the compounds of the invention are also useful in treatment and therapy of proliferative diseases. Particularly, these compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof.

The compounds of the invention can also be used as active agents against solid tumors including, without limitation, a breast tumor, a lung tumor, a colon tumor, a pancreatic tumor, a brain tumor, an ovarian tumor, a gall bladder tumor, an esophaogeal tumor, a cervical tumor, a stomach tumor, a prostate tumor, a thyroid tumor or a combination thereof; malignant ascites; hematopoietic cancers and hyperproliferative disorders such as thyroid hyperplasia (especially Grave's disease); and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention can also be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations

Also embraced within this invention is a class of pharmaceutical compositions, also referred to as medicaments, comprising the active compounds of Formulas I-III in association with one or more non-toxic, pharmaceutically-acceptable carriers and/or diluents and/or adjuvants (collectively referred to herein as "carrier" materials) and, if desired, other active ingredients. The pharmaceutically active compounds of this invention can be processed in accordance with conventional methods of pharmacy to produce medicinal agents for administration to patients, including humans and other mammals.

The compounds of the present invention may be administered to a subject by any suitable route, preferably in the form of a pharmaceutical composition, adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of melanoma and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of cancer, such as with radiation therapy or with neoplastic or cytotoxic agents.

If formulated as a fixed dose, such combination products employ the compounds of this invention within the accepted dosage ranges. Compounds of Formulas I-III may also be administered sequentially with known anticancer or cytotoxic agents when a combination formulation is inappropriate. The invention is not limited in the sequence of administration; compounds of the invention may be administered either prior to, simultaneously with or after administration of the known anticancer or cytotoxic agent.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

Alternatively, the compounds of the invention may also be used in co-therapies with other anti-neoplastic agents, such as other kinase inhibitors including angiogenic agents such as VEGFR inhibitors, p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing is merely illustrative of the invention and is not intended to limit the invention to the disclosed compounds. Variations and changes, which are obvious to one skilled in the art, are intended to be within the scope and nature of the invention, which are defined in the appended claims. All mentioned references, patents, applications and publications, are hereby incorporated by reference in their entirety, as if here written.

What is claimed is:
1. A compound of Formula I:

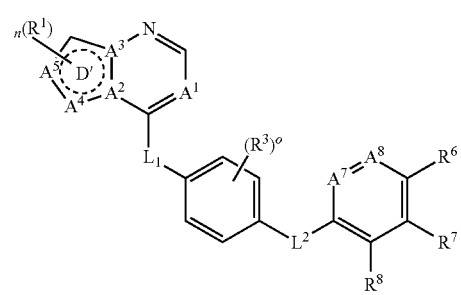

or a stereoisomer or pharmaceutically acceptable salt thereof, wherein
 $A^1$ is $CR^2$;
 D' is a fused heteroaryl ring wherein $A^2$ is N, $A^3$ is C, $A^4$ is N and $A^5$, is $CR^1$;
 each of $L^1$ and $L^2$, independently, is —O—, —$NR^4$—, —S—, —C(O)—, —S(O)—, —$SO_2$— or —$CR^4R^4$—, wherein each $R^4$, independently, is H, halo, OH, $C_{1-6}$alkoxyl, NH—$C_{1-6}$alkyl, CN or $C_{1-6}$alkyl;
 each of $A^7$ and $A^8$, independently, is N or $CR^5$, provided at least one of $A^7$ and $A^8$ is N;
 each $R^1$, independently, is halo, haloalkyl, haloalkoxyl, oxo, CN, OH, SH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl, —$SR^9$, —$OR^9$, —$NR^9R^9$, —$C(O)R^9$, —$COOR^9$, —$OC(O)R^9$, —$C(O)C(O)R^9$, —$C(O)NR^9R^9$, —$NR^9C(O)R^9$, —$NR^9C(O)NR^9R^9$, —$NR^9(COOR^9)$, —$OC(O)NR^9R^9$, —$S(O)_2R^9$, —$S(O)_2R^9$, —$S(O)_2NR^9R^9$, —$NR^9S(O)_2NR^9R^9$, —$NR^9S(O)_2R^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$;
 $R^2$ is H, F, Cl, Br, I, $CF_3$, haloalkyl, CN, OH, SH, $NO_2$, $NH_2$, methyl, ethyl, propyl, methoxy, ethoxy, cyclopropyl or acetyl;
 each $R^3$, independently, is H, F, Cl, Br, $CF_3$, haloalkyl, CN, OH, SH, $NO_2$, $NH_2$, methyl, ethyl, methoxy, ethoxy, cyclopropyl, aminomethyl or acetyl;
 $R^5$ is H or halo;
 $R^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl; and R$^7$ and R$^8$, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of R$^9$;

each R$^9$, independently, is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkenyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, SR$^{10}$, OR$^{10}$, NR$^4$R$^{10}$, C(O)R$^{10}$, COOR$^{10}$, C(O)NR$^4$R$^{10}$, NR$^4$C(O)R$^{10}$, NR$^4$C(O)NR$^4$R$^{10}$, NR$^4$(COOR$^{10}$), S(O)$_2$R$^{10}$, S(O)$_2$NR$^4$R$^{10}$, NR$^4$S(O)$_2$R$^{10}$, NR$^4$S(O)$_2$NR$^4$R$^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl;

R$^{10}$ is H, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl;

n is 0, 1 or 2; and o is 0, 1 or 2, provided the compound is not 4-phenyl-N-(4-(pyrazolo[1,5-a]pyrimidin-7-yl-oxy)phenyl)phthalazin-1-amine.

2. The compound of claim 1, wherein fused ring D' is

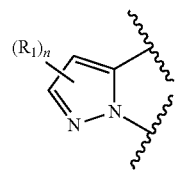

wherein R$^1$ and n are as defined in claim 1;

each of A$^7$ and A$^8$, independently, is N;

L$^1$ is —O—, —S— or —NR$^4$—; and

L$^2$ is —NR$^4$— wherein each R$^4$, independently, is as defined in claim 1.

3. The compound of claim 1, wherein

A$^1$ is CR$^2$;

L$^1$ is —O—, —S— or —NR$^4$—;

L$^2$ is —NR$^4$—; and

R$^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl; and R$^7$ and R$^8$, taken together with the carbon atoms to which they are attached form a phenyl ring optionally substituted independently with 1-4 substituents of R$^9$.

4. The compound of claim 1 having a Formula II:

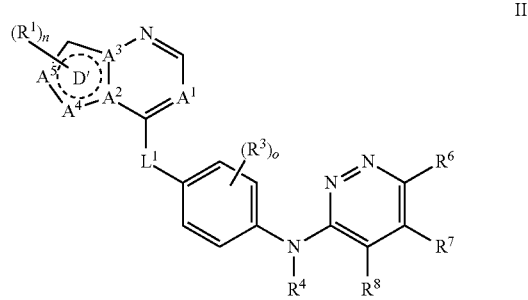

II or a pharmaceutically acceptable salt thereof, wherein

A$^1$ is CR$^2$, and D' is a fused heteroaryl ring wherein A$^2$ is N, A$^3$ is C, A$^4$ is N and A$^5$ is CR$^1$;

L$^1$ is —O—, —S—, or —NR$^4$—;

each R$^1$, independently, is halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, —SR$^9$, —OR$^9$, —NR$^9$R$^9$, —C(O)R$^9$, —COOR$^9$, —OC(O)R$^9$, —C(O)C(O)R$^9$, —C(O)NR$^9$R$^9$, —NR$^9$C(O)R$^9$, —NR$^9$C(O)NR$^9$R$^9$, —NR$^9$(COOR$^9$), —OC(O)NR$^9$R$^9$, —S(O)$_2$R$^9$, —S(O)$_2$R$^9$, —S(O)$_2$NR$^9$R$^9$, —NR$^9$S(O)$_2$NR$^9$R$^9$, —NR$^9$S(O)$_2$R$^9$ or a fully saturated or partially or fully unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^9$;

R$^2$ is H, F, Cl, Br, I, CF$_3$, haloalkyl, CN, OH, SH, NO$_2$, NH$_2$, methyl, ethyl, propyl, methoxy, ethoxy, cyclopropyl or acetyl;

each R$^3$, independently, is H, F, Cl, Br, CF$_3$, haloalkyl, CN, OH, SH, NO$_2$, NH$_2$, methyl, ethyl, methoxy, ethoxy, cyclopropyl, aminomethyl or acetyl;

R$^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl; and R$^7$ and R$^8$, taken together with the carbon atoms to which they are attached form a fully saturated or partially or fully unsaturated 5- or 6-membered ring of carbon atoms optionally including 1-3 heteroatoms selected from O, N, or S, and the ring optionally substituted independently with 1-4 substituents of R$^9$;

each R$^9$, independently, is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxy, SR$^{10}$, OR$^{10}$, NR$^4$R$^{10}$, C(O)R$^{10}$, COOR$^{10}$, C(O)NR$^4$R$^{10}$, NR$^4$C(O)R$^{10}$, NR$^4$C(O)NR$^4$R$^{10}$, NR$^4$(COOR$^{10}$), S(O)$_2$R$^{10}$, S(O)$_2$NR$^4$R$^{10}$, NR$^4$S(O)$_2$R$^{10}$, NR$^4$S(O)$_2$NR$^4$R$^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl;

R$^{10}$ is H, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl;

n is 0, 1, 2 or 3; and o is 0, 1 or 2.

5. The compound of claim 1, having a Formula III:

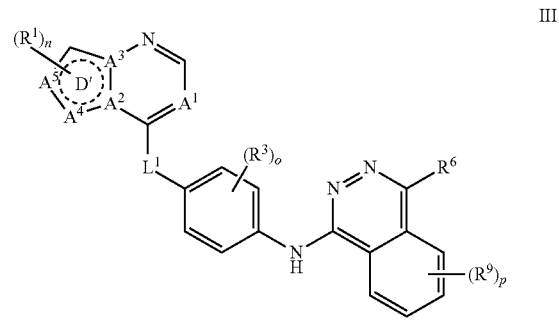

III or a pharmaceutically acceptable salt thereof, wherein

A$^1$ is CR$^2$;

D' is a fused heteroaryl ring wherein A$^2$ is N and A$^3$ is C, and A$^4$ is N and A$^5$, is CR$^1$;

L$^1$ is —O—, —NR$^4$—, —S—, —C(O)—, —S(O)—, —SO$_2$— or —CR$^4$R$^4$—;

each R$^1$, independently, is H, halo, haloalkyl, haloalkoxyl, CN, OH, SH, NO$_2$, NH$_2$, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or —C(O)R$^9$;

R$^2$ is H, F, Cl, Br, I, CF$_3$, haloalkyl, CN, OH, SH, NO$_2$, NH$_2$, methyl, ethyl, propyl, methoxy, ethoxy, cyclopropyl or acetyl;

each R$^3$, independently, is H, F, Cl, Br, CF$_3$, haloalkyl, CN, OH, SH, NO$_2$, NH$_2$, methyl, ethyl, methoxy, ethoxy, cyclopropyl, aminomethyl or acetyl;

R$^4$ is H or C$_{1-6}$alkyl;

R$^6$ is a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of R$^{10}$, halo, haloalkyl, haloalkoxyl, CN, NO$_2$, NH$_2$, OH, oxo, C$_{1-6}$alkyl, C$_{1-6}$alkoxyl, C$_{3-6}$cycloalkyl, C$_{1-10}$-alkylamino-, C$_{1-10}$-dialkylamino-, benzyl or phenyl;

each R$^9$, independently, is H, halo, haloalkyl, haloalkoxyl, oxo, CN, OH, SH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl, SR$^{10}$, OR$^{10}$, NR$^4$R$^{10}$, C(O)R$^{10}$, COOR$^{10}$, C(O)NR$^4$R$^{10}$, NR$^4$C(O)R$^{10}$, NR$^4$C(O)NR$^4$R$^{10}$, NR$^4$(COOR$^{10}$), S(O)$_2$R$^{10}$, S(O)$_2$NR$^4$R$^{10}$, NR$^4$S(O)$_2$R$^{10}$, NR$^4$S(O)$_2$NR$^4$R$^{10}$ or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

$R^{10}$ is H, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl;

n is 0, 1, 2 or 3;
o is 0, 1 or 2; and
p is 0, 1 or 2.

6. The compound of claim 5 wherein $A^1$ is $CR^2$ and D' is a fused heteroaryl ring wherein $A^2$ is N, $A^3$ is C, $A^4$ is N and $A^5$ is $CR^1$; and $R^6$ is phenyl, naphthyl, pyridyl, pyrimidinyl, pyridazinyl, pyazinyl, triazinyl, quinolinyl, dihydroquinolinyl, tetrahydroquinolinyl, isoquinolinyl, tetrahydroisoquinolinyl, quinazolinyl, isoquinazolinyl, phthalazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, hexahydropyrrolo[1,2-a]pyrazinyl, cyclopropyl, cyclobutyl, azetidinyl, cyclopentyl, cyclohexyl, cycloheptyl or pyranyl, each of which is optionally substituted independently with 1-5 substituents of $R^{10}$, halo, haloalkyl, haloalkoxyl, CN, $NO_2$, $NH_2$, OH, oxo, $C_{1-6}$alkyl, $C_{1-6}$alkoxyl, $C_{3-6}$cycloalkyl, $C_{1-10}$-alkylamino-, $C_{1-10}$-dialkylamino-, benzyl or phenyl.

7. The compound of claim 1, or a stereoisomer or pharmaceutically acceptable salt thereof, selected from, 4-(5-chloro-2-pyridinyl)-N-(4-(pyrazolo[1,5-a]pyrimidin-7-ylthio)phenyl)-1-phthalazinamine;

4-(5-methyl-2-pyridinyl)-N-(4-(pyrazolo[1,5-a]pyrimidin-7-ylthio)phenyl)-1-phthalazinamine;

4-(4-chlorophenyl)-N-(4((2-cyclopropylpyrazolo[1,5-a]pyrimidin-7-yl)thio)phenyl)-1-phthalazinamine;

N-(4((2-cyclopropylpyrazolo[1,5-a]pyrimidin-7-yl)thio)phenyl)-4-phenyl-1-phthalazinamine;

N-(4((2-cyclopropylpyrazolo[1,5-a]pyrimidin-7-yl)thio)phenyl)-4-(4-methyl-2-thienyl)-1-phthalazinamine;

4-(4-chlorophenyl)-N-(4-((2-(2-propen-1-yloxy)pyrazolo[1,5-a]pyrimidin-7-yl)sulfanyl)phenyl)-1-phthalazinamine;

N-(4-((2-((2-(methyloxy)ethyl)oxy)pyrazolo[1,5-a]pyrimidin-7-yl)thio)phenyl)-4-phenyl-1-phthalazinamine;

N-(4-((2-((2-(methyloxy)ethyl)oxy)pyrazolo[1,5-a]pyrimidin-7-yl)thio)phenyl)-4-(4-methyl-2-thienyl)-1-phthalazinamine;

4-(4-chlorophenyl)-N-(4-((2-((2-(methyloxy)ethyl)oxy)pyrazolo[1,5-a]pyrimidin-7-yl)thio)phenyl)-1-phthalazinamine; and 7-((4-((4-(4-chlorophenyl)-1-phthalazinyl)amino)phenyl)thio)pyrazolo[1,5-a]pyrimidin-2-ol.

8. A pharmaceutical composition comprising a pharmaceutically acceptable excipient and an effective dosage amount of the compound of claim 1.

9. A pharmaceutical composition comprising a pharmaceutically acceptable excipient and an effective dosage amount of the compound of claim 4.

10. A pharmaceutical composition comprising a pharmaceutically acceptable excipient and an effective dosage amount of the compound of claim 5.

11. A method of making a compound of claim 1, the method comprising the step of reacting compound of Formula A

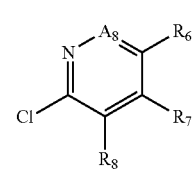

with a compound of Formula B

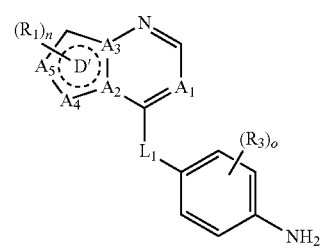

wherein $A^8$ and $R^{6-8}$ of the compound of formula A and $A^1$, $A^2$, $A^3$, $A^4$, $A^5$, $L^1$, $R^1$, $A^3$ and n and o of the compound of formula B are as defined in claim 1, to make a compound of Formula I.

* * * * *